United States Patent [19]
Millard et al.

[11] Patent Number: 5,534,416
[45] Date of Patent: *Jul. 9, 1996

[54] FLUORESCENT VIABILITY ASSAY USING CYCLIC-SUBSTITUTED UNSYMMETRICAL CYANINE DYES

[75] Inventors: Paul J. Millard, Eugene; Bruce L. Roth, Corvallis; Stephen T. Yue; Richard P. Haugland, both of Eugene, all of Oreg.

[73] Assignee: Molecular Probes, Inc., Eugene, Oreg.

[*] Notice: The term of this patent shall not extend beyond the expiration date of Pat. No. 5,372,842.

[21] Appl. No.: 148,847

[22] Filed: Nov. 8, 1993

Related U.S. Application Data

[63] Continuation of Ser. No. 90,890, Jul. 12, 1993, Pat. No. 5,436,134, and Ser. No. 146,328, Nov. 1, 1993, each is a continuation-in-part of Ser. No.47,683, Apr. 13, 1993, abandoned.

[51] Int. Cl.$^6$ .............................. G01N 33/00; C12Q 1/04; C12Q 1/68; C07H 1/00
[52] U.S. Cl. .................. 436/34; 436/94; 436/63; 436/800; 435/34; 435/29; 435/4; 435/6; 536/26.73; 536/1.11
[58] Field of Search .................. 436/34, 94, 63, 436/800; 435/29, 34, 4, 6; 536/26.73, 1.11

[56] References Cited

U.S. PATENT DOCUMENTS

| | | | |
|---|---|---|---|
| 4,190,328 | 2/1980 | Levine et al. | 350/320 |
| 4,544,546 | 10/1985 | Wang et al. | 424/7.1 |
| 4,665,024 | 5/1987 | Mansour | 435/34 |
| 4,883,867 | 11/1989 | Lee et al. | 436/63 |
| 4,937,198 | 6/1990 | Lee et al. | 436/94 |
| 5,057,413 | 10/1991 | Terstappen et al. | 435/6 |
| 5,208,148 | 5/1993 | Naleway et al. | 436/34 |
| 5,242,805 | 7/1993 | Naleway et al. | 435/18 |

FOREIGN PATENT DOCUMENTS

| | | |
|---|---|---|
| 0410806A1 | 1/1991 | European Pat. Off. . |
| 0453197A1 | 10/1991 | European Pat. Off. . |
| 2074340 | 10/1981 | United Kingdom . |
| WO93/04074 | 3/1993 | WIPO . |
| WO93/04192 | 3/1993 | WIPO . |
| 9306482 | 4/1993 | WIPO . |
| WO93/06482 | 4/1993 | WIPO . |

OTHER PUBLICATIONS

Johnson et al; Fed Am Soc Exp Biol, J 6(1) 1992 (A314).
Nucleic acids research, vol. 20, No. 11, pp. 2803–2812.
Kudinova, et al., Chemical Abstracts 93:241180j (1993).
Kudinova, et al. Khim. Geterotsikl. Soedin. 7, 903 (1980).
Simbera, et al., Chemical Abstracts 89:112299y (1978).
Haugland, Handbook of Fluorescent Probes and Research Chemicals Sets 25 & 31 (1992).
Kaneshiro, et al., J. Microbiolog. Methods 17, 1 (1993).
Brooker, et al., J. Am. Chem. Soc. 64, 199 (1942).
Griffiths, Colour and Constitution of Organic Molecules, p. 241 Academic Press (1976).
Heterocyclic Compounds, vol. 4, R. C. Elderfield ed., John Wiley and Sons Inc., (1952) pp. 1–331.
Wawzonek, et al., J. Heterocyclic Chem., 25, 381 (1988).
Watkins, J. Chem. Soc. 3059 (1952).
Marson, Tetrahedron, 48, 3659 (1992).
Rye, et al., Nucleic Acid Res., 20, 2083 (1992).

*Primary Examiner*—John Kight
*Assistant Examiner*—Louise N. Leary
*Attorney, Agent, or Firm*—Allegra J. Helfenstein; Anton E. Skaugset

[57] ABSTRACT

The invention relates to a method of analyzing the viability of a sample of cells using an aqueous solution comprising two fluorescent dyes. Dye I has the formula:

(Abstract continued on next page.)

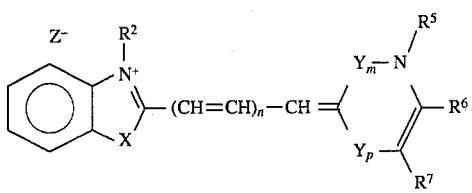

where $R^2$ is $C_{1-6}$ alkyl; $Z^-$ is a biologically compatible counterion;

X is O; S; Se; or $NR^{15}$, where $R^{15}$ is H or $C_{1-6}$ alkyl; or $CR^{16}R^{17}$, where $R^{16}$ and $R^{17}$, which may be the same or different, are independently H or $C_{1-6}$ alkyl, or the carbons of $R^{16}$ and $R^{17}$ taken in combination complete a five or six membered saturated ring; and the benzazolium is optionally further substituted;

n=0, 1, or 2;

Y is $-CR^3=CR^4-$; p and m=0 or 1, such that p+m=1;

$R^5$ is a $C_{1-6}$ alkyl, $C_{1-6}$ alkenyl, $C_{1-6}$ polyalkenyl, $C_{1-6}$ alkynyl or $C_{1-6}$ polyalkynyl group; or $R^5$ is an OMEGA;

$R^3$, $R^4$, $R^6$ and $R^7$, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or halogen; or $-OR^8$, $-SR^8$, $-(NR^8 R^9)$, where $R^8$ and $R^9$, which may be the same or different, are independently H; or alkyl groups having 1–6 carbons; or 1–2 substituted or unsubstituted alicyclic, heteroalicyclic, aromatic, or heteroaromatic rings, containing 1–4 heteroatoms, wherein the heteroatoms are O, N, or S; or $R^8$ and $R^9$ taken in combination are $-(CH_2)_2-L-(CH_2)_2-$ where L=$-O-$, $-NR^{10}-$, $-CH_2-$ or a single bond where $R^{10}$ is H or an alkyl group having 1–6 carbons; or $-OSO_2R^{19}$ where $R^{19}$ is $C_{1-6}$ alkyl, or $C_{1-6}$ perfluoroalkyl, or aryl; or an OMEGA; or $R^6$ and $R^7$, taken in combination are $-(CH_2)_v-$ where v=3 or 4, or $R^6$ and $R^7$ form a fused aromatic ring that is optionally further substituted;

such that at least one of $R^3$, $R^4$, $R^5$, $R^6$ and $R^7$, or a substituent on the aromatic ring formed by $R^6$ and $R^7$, is an OMEGA; where OMEGA is a cyclic substituent that is attached by a single bond.

Fluorescent Dye II selectively stains either viable or non-viable cells with a detectable fluorescent response that is different from the fluorescent response of Dye I. The stained cells are illuminated at a suitable absorption wavelength, and the fluorescent response is detected to distinguish viable and non-viable cells based on the fluorescent response.

20 Claims, 4 Drawing Sheets

Figure 4a)-4b)
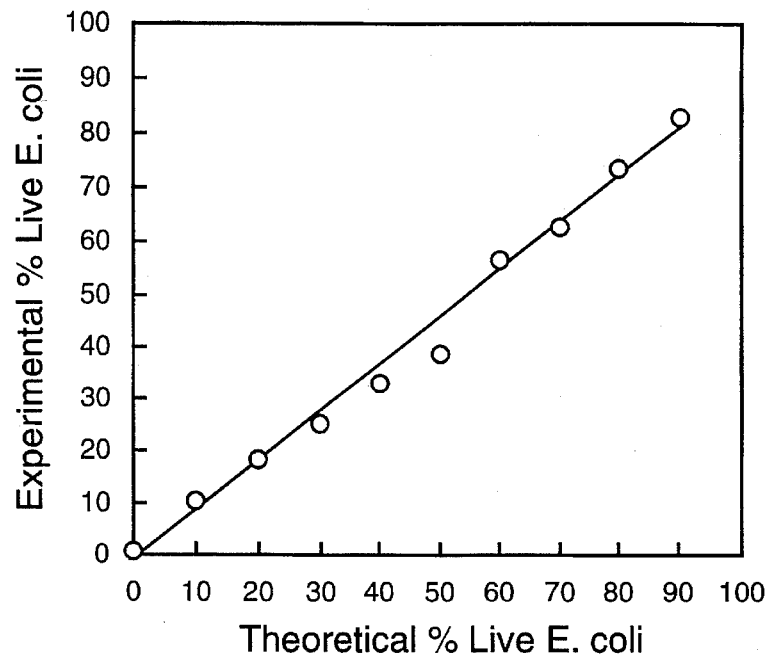
Figure 4a)
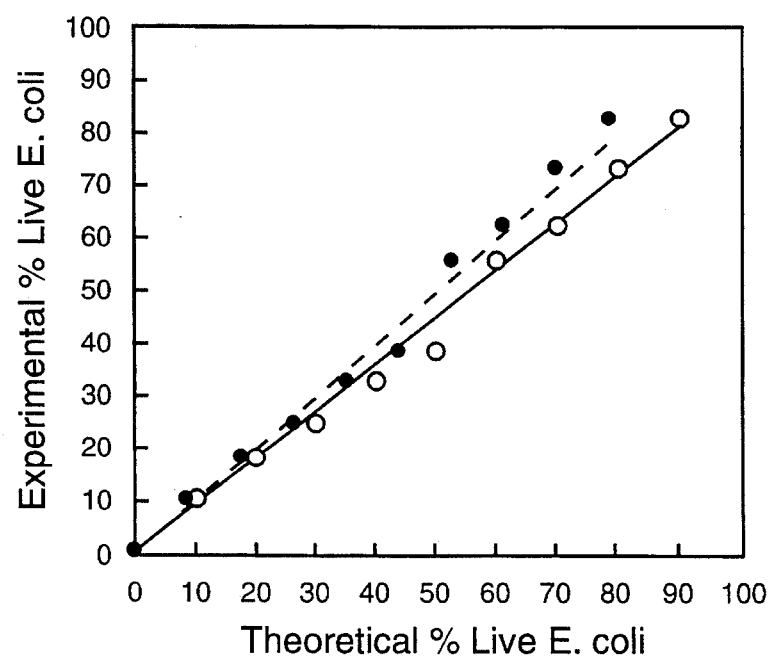
Figure 4b)

FLUORESCENT VIABILITY ASSAY USING CYCLIC-SUBSTITUTED UNSYMMETRICAL CYANINE DYES

This application is a continuation-in-part of patent application Ser. No. 08/090,890 filed Jul. 12, 1993 now U.S. Pat. No. 5,436,134 and a continuation in part of FLUORESCENT ASSAY FOR BACTERIAL GRAM REACTION copending U.S. patent application Ser. No. 08/146,328, filed Nov. 1, 1993 by Roth, et al.; both of which are continuations-in-part of patent application Ser. No. 08/047,683 filed Apr. 13, 1993, now abandoned.

FIELD OF THE INVENTION

The invention relates to a fluorescence assay that permits the simultaneous or sequential determination of live and dead cells. In particular, the invention relates to the use of a combination of two fluorescent dyes, where one fluorescent dye is a cyclic-substituted unsymmetrical cyanine dye and stains the nucleic acids of all cells, and the other fluorescent dye has spectral properties that are detectably different from those of the first dye and is selective for either live or for dead cells.

BACKGROUND OF THE INVENTION

Evaluation of cell viability is important for assessing the effect of drugs, environmental pollutants, irradiation, temperature, ionic extremes, and other potential biological modifiers. Traditionally, cell membrane integrity is used as an indicator of cell viability, as damage to the protective cell membrane often results in loss of cell structure, leakage of critical intracellular contents, breakdown of essential ionic gradients and ultimately cell death. Another indicator of cell viability is intracellular activity, the presence of which activity indicates that the cell is able to metabolize, grow, reproduce, maintain electrical membrane potential, or perform some other cell function critical for viability. Conversely, the lack of such activity is often used as an indicator of cell death.

Although a single dye can be used to assess viability, the use of a combination of dyes has advantages. First, the use of a dye combination allows the investigator to determine the ratio of the number of cells that show a response to the one dye versus the total number of cells or versus those cells that do not respond. In addition, the second dye can be used as a positive control to indicate that other cells are present that did not stain with the first dye. For this reason, methods of determining viability that use a combination of dyes are generally preferred.

Several methods using a combination of fluorescent dyes for the analysis of cell viability have been developed, including methods that use differential fluorescent staining of live and dead cells. Haugland, HANDBOOK OF FLUORESCENT PROBES AND RESEARCH CHEMICALS Sets 25 & 31 (1992) (incorporated by reference). Live, intact cells can generally be distinguished from dead cells with compromised membranes by differential staining using a cell-impermeant fluorescent dye that only enters dead cells, and a cell-permeant dye that enters both live and dead cells but requires intracellular activity indicative of viability for the production of fluorescence. Alternatively, differential fluorescent staining can involve the use of two cell-permeant dyes where one stains both live and dead cells and the other stains cells only when an intracellular reaction produces fluorescence.

Not all fluorescent compounds that have these general characteristics are equally useful, however. A number of fluorescent viability stains, for example, have spectral or physical properties that are incompatible with available instrumentation or limit their use in conjunction with other materials. For instance, the use of acridine orange (U.S. Pat. No. 4,190,328) is severely limited because of high background signal and low fluorescence enhancement upon binding to nucleic acids (about two-fold). Nucleic acids complexed with DAPI or Hoechst 3342 are only excitable with UV light, which is incompatible with some instrumentation. More importantly, the spectral properties of DAPI- or Hoechst 33342-bound DNA overlap significantly with cellular autofluorescence.

Moreover, it is not uncommon that fluorescent materials that are useful with one type of cell, or will not produce the desired reaction in different types of cells. For example, calcein-AM and ethidium homodimer (Ser. No. 07/783,182 (filed Oct. 26, 1991) to Haugland et al.) now U.S. Pat. No. 5,314,805, have been found to be less useful with cells from prokaryotic microbes than with those of eukaryotic microbes (Kaneshiro, et al., J. MICROBIOLOG. METHODS 17, 1 (1993)).

The method of the present invention provides significant advantages over conventional methods. This method, which allows the determination of cell viability either simultaneously or sequentially, is applicable to a wide range of cells, regardless of the source. In addition, the availability of a family of dyes with similar permeability characteristics but different spectral characteristics allows the selection of complementary pairs impermeant and permeant stains. Furthermore, the method is extremely sensitive, reliable and fast, requiring no harsh reagents or special culturing conditions. It is useful for laboratory analysis, industrial process monitoring and environmental sampling.

The method of the invention utilizes a fluorogenic dye from a new family of unsymmetrical cyanine dyes that was unexpectedly found to label all cells tested, whether living or dead, described in copending applications Ser. No. 08/090,890, filed Jul. 12, 1993, now U.S. Pat. No. 5,436,134, by Haugland, et al. and FLUORESCENT ASSAY FOR BACTERIAL GRAM REACTION, filed Nov. 1, 1993 by Roth, et al.; both of which are continuations-in-part of patent application Ser. No. 08/047,683, filed Apr. 13, 1993, now abandoned, by Roth et al. (all three of which are incorporated by reference). Although certain unsymmetrical cyanine dyes were first described before the genetic role of nucleic acids was established (Brooker, et al., J. Am. Chem. Soc. 64, 199 (1942)), a variety of unsymmetrical cyanine dyes have now been found to be very effective in the fluorescent staining of DNA and RNA. U.S. Pat. Nos. 4,554,546 (to Wang, et al. 1985) and 5,057,413 (to Terstappen et al. 1991) disclose use of similar derivatives of thioflavins as nucleic acid stains. U.S. Pat. No. 4,937,198 (to Lee et al. 1990) discloses a fluorescent nucleic acid stain that preferentially stains the nucleic acids of bloodborne parasites with little staining of nucleated blood cells.

Closely related lower alkyl (1–6 carbons) substituted unsymmetrical cyanine dyes, exemplified by thiazole orange, are disclosed in U.S. Pat. No. 4,883,867, as having particular advantages in reticulocyte analysis. The attachment of bulkier (e.g. cyclic) structures to the parent unsymmetrical cyanine dye results in a number of unexpected advantages for this family of dyes. For example, although bulkier, the new dyes more quickly penetrate the cell membranes of a wider variety of cell types, including both Gram-positive and Gram-negative bacteria, as well as a variety of eukaryotic cells. Direct comparison of the rate of uptake with known dyes such as thiazole orange and its alkylated derivatives, shows enhanced uptake of the new compounds (FIG. 1). Moreover, a wider range of cells stained with the novel dyes generally exhibit much more fluorescence than cells stained with thiazole orange (Table 1), and the quantum yield of these new dyes is unexpectedly better than that of thiazole orange (Table 2). Furthermore, by simple synthetic modification, a family of dyes having absorption and emission spectral properties that cover most of the visible and near-infrared spectrum can be prepared. These features overcome the limitations imposed by thiazole orange and other unsymmetrical cyanine dyes for staining the nucleic acids of a wide variety of cells. The superior properties exhibited by these dyes were neither anticipated nor obvious in view of the known unsymmetrical cyanine dyes.

that stains all cells in the sample. The other dye used for the invention (Dye II) is a fluorescent dye that selectively stains either viable or non-viable cells in the sample and gives a fluorescent response that is different from that of Dye I. When Dyes I and II are added to the sample of cells being analyzed, viable cells have one staining pattern, non-viable cells have a detectably different staining pattern. Using fluorescent detection techniques, this method is used to determine the viability of the cells in the sample, and optionally to sort the cells.

Dye I

Dye I is lightly colored and is virtually non-fluorescent when diluted in aqueous solution according to the method of the invention. Dye I is highly membrane-permeant and labels all cells, whether live or dead. When Dye I binds with intracellular nucleic acid polymers such as DNA and RNA, the resultant dye-nucleic acid complex becomes extremely

TABLE 1

| Sample[3] | Fluorescence/Cell (ex 485/em 530)[1] | | | | | | | | |
|---|---|---|---|---|---|---|---|---|---|
| | Dye[2] | | | | | | | | |
| | 61 | 63 | 613 | 619 | 624 | 628 | 591 | 634 | Thiazole Orange |
| B. cereus | 196 | 93 | 242 | 827 | 709 | 613 | 58 | 154 | 51 |
| M. luteus | 49 | 33 | 75 | 149 | 162 | 149 | 375 | 58 | 21 |
| S. pyogenes | 0.01 | 0.01 | 0.02 | 0.06 | 0.05 | 0.04 | <0.01 | 0.03 | <0.01 |
| S. aureus | 15 | 5 | 10 | 47 | 44 | 34 | 3 | 15 | 3.2 |
| E. coli | 10 | 6 | 12 | 26 | 24 | 28 | 2 | 4 | 2 |
| S. oranienburg | 10 | 4 | 10 | 18 | 15 | 19 | 2 | 5 | 1 |
| K. pneumonia | 10 | 5 | 10 | 12 | 17 | 20 | 2 | 4 | 3 |
| S. sonnei | 6 | 3 | 6 | 13 | 11 | 16 | 1 | 4 | 1 |
| P. aeruginosa | 5 | 3 | 6 | 16 | 14 | 14 | 1 | 3 | 2 |

1. Measured in a fluorescence microtiter plate reader with extraction and emission filters at 485+/−10 and 530+/−12, respectively. Fluorescence data are corrected for cell number; but are not corrected for cell volume or nucleic acid content.
2. Optimal dye concentrations determined as in Example 3.
3. Suspension concentrations as used for Example 3.

DESCRIPTION OF THE DRAWINGS

FIG. 4a)–4b): The correspondence between experimental and theoretical live/dead ratios determined using flow cytometric analysis of mixed live and dead samples of E. coli stained with dye 624 and propidium iodide. FIG. 4a) shows the uncorrected calibration curve. FIG. 4b) shows the calibration curve after inclusion of a correction factor (the assumption that the "live" population includes 13% dead bacteria) (See Example 8).

SUMMARY OF THE INVENTION INCLUDING DESCRIPTION OF PREFERRED EMBODIMENTS

Figure 1:
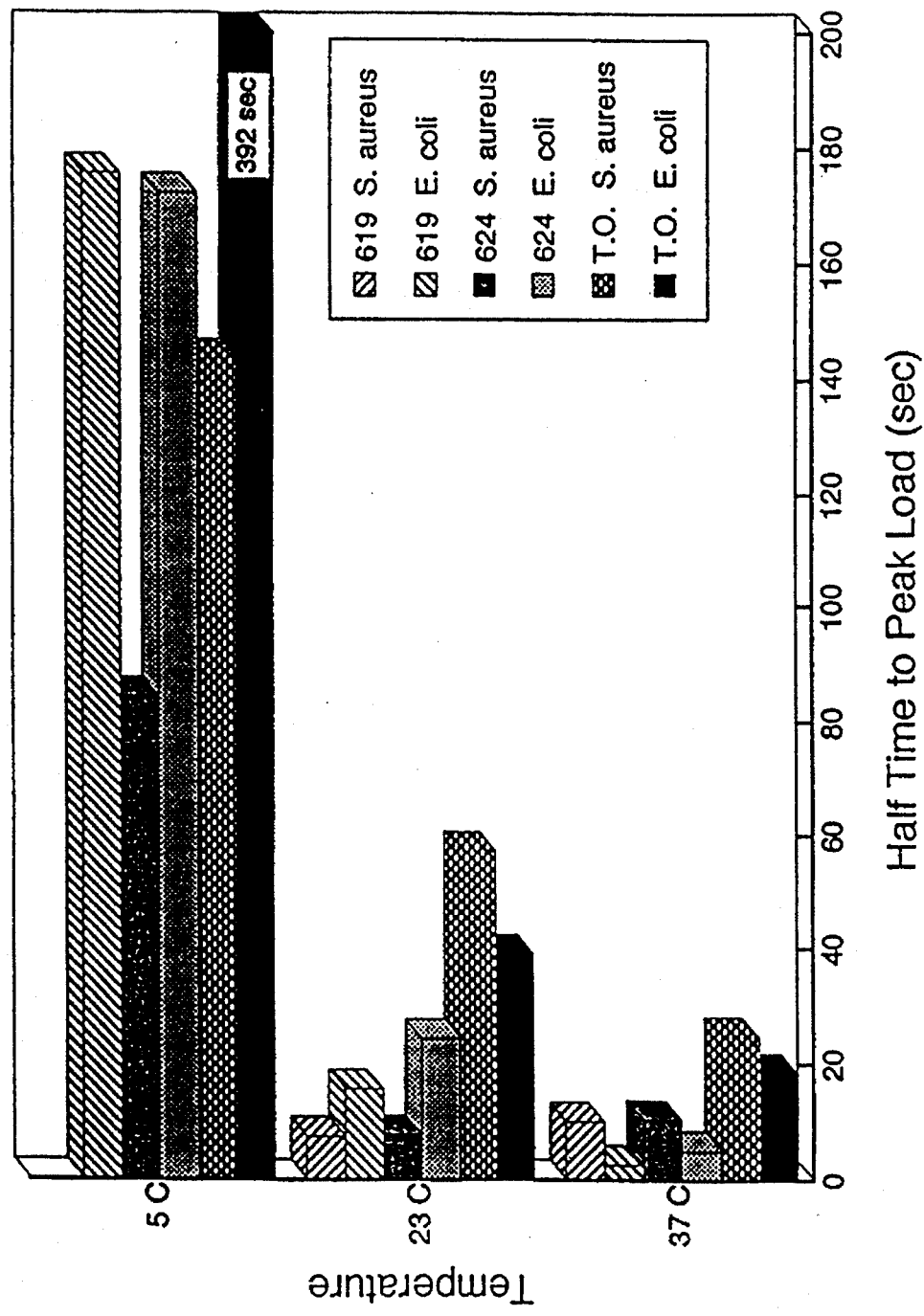
FIG. 1: A comparison of loading times for specific Dye I dyes vs. Thiazole Orange (Example 4).

The invention relates to a method of analyzing the viability of cells using two fluorescent dyes, where one of the dyes (Dye I) is a cyclic-substituted unsymmetrical cyanine dye fluorescent upon illumination. The quantum yield of the preferred Dye I/DNA complex is greater than 0.02, typically greater than 0.1, preferably greater than 0.2, and more preferably greater than 0.3. Typically, Dye I combines with intracellular nucleic acids to give a green or red fluorescence. When excited at a wavelength between about 300 nm and about 500 nm, the dyes complexed with nucleic acids have an emission maximum between about 500 and about 610 nm (see Table 2). Preferably, Dye I complexed with nucleic acids has an emission maximum of between about 500 nm and about 535 nm, resulting in a true green fluorescent signal in cells of the sample where Dye I is present alone.

The cyclic-substituted unsymmetrical cyanine dye (Dye I) for use in this invention has the formula:

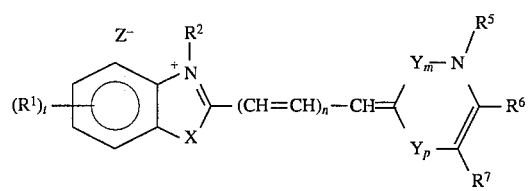

The formula of Dye I can be considered in three parts: 1) A first heterocyclic ring system that is a substituted benzazolium ring system, 2) a linking methine bridge and 3) a second heterocyclic ring system that is a pyridinium or quinolinium ring system, one or more substituents of which must be an OMEGA.

An OMEGA is a saturated or unsaturated, substituted or unsubstituted, cyclic substituent that has a total of 2–16 ring carbon atoms in 1–2 alicyclic, heteroalicyclic, aromatic, or heteroaromatic rings containing 1–4 heteroatoms (wherein the hetero atoms are O, N or S) that is directly bonded to the pyridinium or quinolinium ring system by a single bond. OMEGAs that are alicyclic ring systems may be either linked or fused. Examples of OMEGA are substituted or unsubstituted cyclohexyls, cyclohexenyls, morpholinyls, and piperidinyls. Examples of OMEGA that are aromatic include substituted or unsubstituted naphthyls, phenyls, thienyls, benzothiazolyls, furanyls, oxazolyls, benzoxazolyls, and pyridinyls. Substituents on OMEGA are independently hydrogen, halogen, alkyl, perfluoroalkyl, amino, alkylamino, dialkylamino, alkoxy or carboxyalkyl, each alkyl having 1–6 carbons. Preferred embodiments of OMEGA are substituted or unsubstituted naphthyl, phenyl, thienyl, morpholinyl, and cyclohexyl, more preferably substituted or unsubstituted phenyl.

Although $R^1$ on the benzazolium ring system is usually H, incorporation of a non-hydrogen substituent $R^1$ can be used to fine tune the absorption and emission spectrum of the resulting dye. For instance when $R^1$ is methoxy (compound 770) its absorption spectrum shifts ~12 nm and its emission spectrum shifts ~18 nm (Table 2) relative to the comparable compound where $R^1$ is H (compound 63). The benzazole may contain more than one substituent $R^1$, which may be the same or different (t=1–4). Each $R^1$ is optionally an alkyl group having from 1–6 carbons; or a trifluoromethyl; or a halogen; or —$OR^8$, —$SR^8$ or —$(NR^8R^9)$ where $R^8$ and $R^9$, which can be the same or different, are independently H or alkyl groups having 1–6 carbons; or 1–2 alicyclic, heteroalicyclic, aromatic, or heteroaromatic rings having a total of 3–16 ring atoms (wherein the hetero atoms are O, N or S); or $R^8$ and $R^9$ taken in combination are —$(CH_2)_2$—L—$(CH_2)_2$— where L=—O—, —$NR^{10}$, —$CH_2$— or a single bond where $R^{10}$ is H or an alkyl group having 1–6 carbons. Typically, the compound contains no more than one $R^1$ that is not H.

The substituent $R^2$ is an alkyl group having 1–6 carbons, preferably methyl or ethyl, more preferably methyl.

The counterion $Z^-$ is a biologically compatible ion that is stable and synthetically accessible. As used herein, a substance that is biologically compatible is not toxic as used, and does not have a substantially deleterious effect on biomolecules. Examples of $Z^-$ include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred $Z^-$ counterions are chloride, iodide, perchlorate and various sulfonates.

X is one of O, S, Se or $NR^{15}$, where $R^{15}$ is H or an alkyl group having 1–6 carbons. Preferably, X is O or S. Alternatively, X is $CR^{16}R^{17}$, where $R^{16}$ and $R^{17}$, which may be the same or different, are independently H or alkyl groups having 1–6 carbons, or the carbons of $R^{16}$ and $R^{17}$ taken in combination complete a five or six membered saturated ring. Generally, $R^{16}$ and $R^{17}$ are methyls.

The methine bridge consists of 1, 3 or 5 methine (—CH=) groups that bridge the benzazolium portion of the molecule and the pyridinium portion in such a way as to permit extensive electronic delocalization. When n=0 the dyes are unsymmetrical monomethine dyes that generally stain with a green fluorescence; when n=1 the dyes are trimethine dyes that generally stain with a red fluorescence; when n=2, the dyes are pentamethine dyes that generally stain with a non-visible, near infrared fluorescence. It has been recognized from studies involving similar compounds that the number of methine groups between the heteroaromatic rings has a considerable influence on the spectral properties of the dye (Griffiths, COLOUR AND CONSTITUTION OF ORGANIC MOLECULES, pp. 241 Academic Press (1976)). Additional non-hydrogen substituents on the heterocyclic ring systems further affect the spectral properties of the dyes. This is demonstrated for the subject dyes in Table 2, below.

The N-bound substituent $R^5$ is an alkyl, alkenyl, polyalkenyl, alkynyl or polyalkynyl group having 1–6 carbons; or $R^5$ is an OMEGA. Most commonly $R^5$ is an OMEGA.

The pyridinium or quinolinium ring system contains a ring fragment Y that is —$CR^3$=$CR^4$—, with subscripts p and m equal to 0 or 1, such that p+m=1. For all embodiments, the ring contains a 6 membered pyridinium-based heterocycle according to one of these formulations

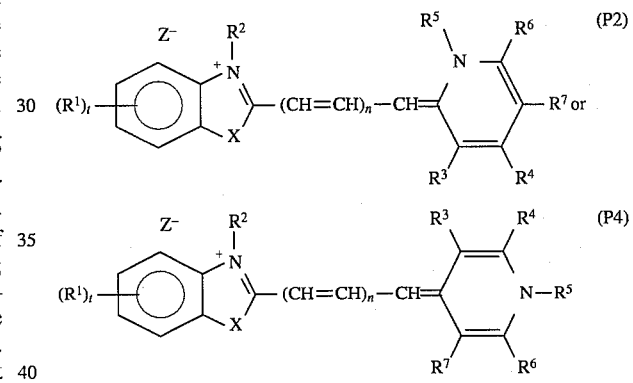

In preferred embodiments of the invention, m=1 and p=0 (4-pyridinium) (P4).

The substituents on the second heterocyclic ring system, $R^3$, $R^4$, $R^6$ and $R^7$, may be the same or different and are independently H; or an alkyl, alkenyl, polyalkenyl, alkynyl or polyalkynyl group having 1–6 carbons; or a halogen; or —$OR^8$, —$SR^8$, —$(NR^8R^9)$, as defined previously; or —$OSO_2R^{19}$ where $R^{19}$ is alkyl having 1–6 carbons, or perfluoroalkyl having 1–6 carbons, or aryl; or an OMEGA (defined above); or $R^6$ and $R^7$ taken in combination are —$(CH_2)_v$— where v=3 or 4, forming a fused 5 or 6 membered ring, or $R^6$ and $R^7$, taken in combination form a fused 6 membered aromatic ring. Typically, $R^3$, $R^4$, $R^6$ and $R^7$ are independently H, halogen, alkyl, or —$OR^8$, —$SR^8$, —$(NR^8R^9)$, where $R^8$ and $R^9$ are methyl or ethyl; or an OMEGA, or $R^6$ and $R^7$, taken in combination form a fused 6 membered aromatic ring.

Where $R^6$ and $R^7$ taken in combination form a fused 6 membered aromatic ring, embodiments of this invention are quinolinium derivatives containing a fused aromatic ring according to the formula

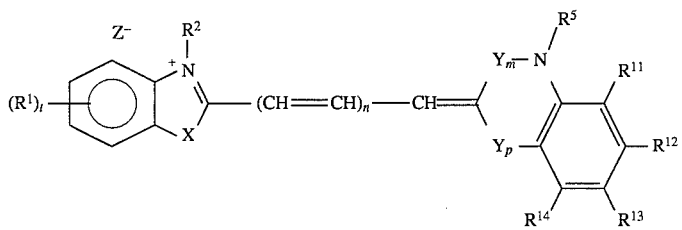

where ring substituents $R^{11}$, $R^{12}$, $R^{13}$, and $R^{14}$ may be the same or different, and are independently H; or an alkyl, alkenyl, polyalkenyl, alkynyl or polyalkynyl group having 1–6 carbons; or a halogen; or —OH, —$OR^8$, —$SR^8$, —($NR^8R^9$), where $R^8$ and $R^9$ are as defined previously; or —$OSO_2R^{19}$ where $R^{19}$ is alkyl having 1–6 carbons, or perfluoroalkyl having 1–6 carbons, or aryl; or an OMEGA. A preferred embodiment of the invention is a quinolinium wherein m=1 and p=0 (4-quinolinium) (see P4 above). Typically the ring substituents are independently H, halogen, alkyl, or —$OR^8$, —$SR^8$, —($NR^8R^9$), where $R^8$ and $R^9$ are methyl or ethyl; or an OMEGA.

For all embodiments of the invention, one or more of the substituents of the pyridinium or quinolinium ring system must be an OMEGA. Preferably, one or two substituents are OMEGAs. When more than one OMEGA is bound to a compound of the present invention, the two or more OMEGAs may be the same or different. For embodiments of the invention that contain pyridinium ring systems, OMEGA is preferably $R^5$, or $R^6$ or both. For embodiments of the invention that contain a 4-quinolinium ring system, OMEGA is preferably $R^4$ or $R^5$, or both. For embodiments of the invention that contain a 2-quinolinium ring system, OMEGA is preferably $R^5$, $R^{11}$ or both. For all embodiments of the invention, preferably $R^5$ is an OMEGA.

One embodiment of the invention contains exactly two non-hydrogen substituents on the second heterocyclic ring, one of which is an OMEGA. In preferred embodiments, $R^5$ is an OMEGA. In additional preferred embodiments of the invention, $R^5$ is an OMEGA and the substituent adjacent to $R^5$ ($R^6$ for pyridiniums, $R^4$ for 4-quinoliniums, and $R^{11}$ for 2-quinoliniums) is a non-hydrogen substituent. In one embodiment the substituent adjacent to $R^5$ is halogen, —$OR^8$, —$SR^8$, —$NR^8R^9$, or —$OSO_2R^{19}$, more preferably halogen. In another embodiment of the invention, $R^5$ is —$OR^8$, —$SR^8$, or —$NR^8R^9$, preferably —$NR^8R^9$. In yet another embodiment of the invention, the substituent adjacent to $R^5$ is an OMEGA. $R^8$ and $R^9$ are as defined previously.

TABLE 2

| DYE | EX max/EM max | QY[†] (DNA) | Kp* |
|---|---|---|---|
| Thiazole Orange | 510/530 | 0.18 | 4.8 E6 |
| 61 | 500/527 | 0.46 | 1.0 E7 |
| 63 | 514/531 | 0.24 | 3.9 E6 |
| 64 | 450/523 | | |
| 71 | 508/526 | 0.31 | |
| 72 | 515/535 | 0.026 | 1.2 E6 |
| 73 | 508/525 | 0.31 | 4.4 E6 |
| 200 | 739/759 | | |
| 542 | 510/527 | | |
| 578 | 470/504 | | 4.1 E5 |
| 582 | 516/533 | | |
| 591 | 509/532 | 0.09 | 4.8 E6 |
| 613 | 506/523 | 0.33 | 5.3 E6 |

TABLE 2-continued

| DYE | EX max/EM max | QY[†] (DNA) | Kp* |
|---|---|---|---|
| 616 | 471/510 | | 3.8 E5 |
| 619 | 488/517 | 0.62 | 9.7 E6 |
| 621 | 635/656 | | |
| 624 | 480/501 | 0.58 | 5.0 E6 |
| 628 | 488/506 | 0.40 | 7.0 E6 |
| 630 | 517/544 | 0.19 | |
| 633 | 489/508 | 0.12 | 7.4 E5 |
| 634 | 510/530 | 0.18 | 2.0 E6 |
| 637 | 601/622 | 0.28 | |
| 639 | 513/548 | 0.20 | 8.0 E6 |
| 640 | 471/516 | | |
| 641 | 503/526 | 0.35 | 2.0 E7 |
| 672 | 586/611 | | |
| 720 | 487/507 | 0.52 | 1.2 E7 |
| 742 | 570/611 | | |
| 752 | 494/518 | 0.51 | |
| 758 | 504/524 | 0.44 | 8.5 E6 |
| 760 | 485/510 | 0.68 | |
| 764 | 486/508 | 0.58 | 1.1 E7 |
| 765 | 506/524 | 0.50 | 1.1 E7 |
| 770 | 526/549 | | 1.7 E6 |
| 774 | 517/533 | | 7.9 E6 |
| 776 | | 0.65 | |
| 780 (Cl) | 513/536 | 0.09 | 3.4 E6 |
| 780 (S) | | 0.31 | |
| 830 | 517/533 | | |
| 834 | 486/507 | | |
| 835 | 495/518 | | |
| 853 | 516/555 | | |
| 854 | 483/520 | | |
| 856 | 502/523 | 0.43 | |
| 5103 | 511/530 | 0.18 | 5.4 E6 |
| 6104 | 505/523 | 0.52 | 1.3 E7 |

[†]Quantum yield (QY) of dye on DNA (standard solution in Tris buffered saline adjusted to pH 10) in comparison with fluorescein, which is assumed to have a quantum yield of 0.92 under the test conditions.
*The dye's DNA partition coefficient ($K_p$) was determined in a 10% ethanol/water solution by linear fitting of plots of reciprocal fluorescence enhancement versus reciprocal DNA concentration as in Example 11.

TABLE 3

| DYE | X | heterocycle | R¹ | R² | R⁴ | R⁵ | R¹¹ | R¹² | n |
|---|---|---|---|---|---|---|---|---|---|
| 125 | S | 2-pyridinium | H | Me | H | phenyl | — | — | 0 |
| 578 | S | 4-pyridinium | H | Me | Cl | phenyl | — | — | 0 |
| 616 | S | 4-pyridinium | H | Me | Cl | o-MeO-phenyl | — | — | 0 |
| 640 | S | 4-pyridinium | H | Me | H | phenyl | — | — | 0 |
| 742 | S | 4-pyridinium | H | Me | n-butyl | phenyl | — | — | 1 |
| 64 | S | 2-quinolinium | H | Me | H | phenyl | H | H | 0 |
| 61 | S | 4-quinolinium | H | Me | n-butyl | phenyl | H | H | 0 |
| 63 | S | 4-quinolinium | H | Me | H | phenyl | H | H | 0 |
| 71 | S | 4-quinolinium | H | Me | n-butyl | thienyl | H | H | 0 |
| 72 | S | 4-quinolinium | H | Me | H | Me | phenyl | H | 0 |
| 73 | S | 4-quinolinium | H | Me | H | cyclohexyl | H | H | 0 |
| 130 | S | 4-quinolinium | H | Me | —NH-phenyl | phenyl | H | H | 0 |
| 100 | S | 4-quinolinium | H | Me | n-butyl | phenyl | H | H | 2 |
| 200 | S | 4-quinolinium | H | Et | Cl | phenyl | H | H | 0 |
| 542 | S | 4-quinolinium | H | Me | H | cyclohexyl | H | H | 0 |
| 582 | S | 4-quinolinium | H | Me | Cl | p-MeO-phenyl | H | H | 0 |
| 591 | S | 4-quinolinium | H | Me | Cl | phenyl | H | H | 0 |
| 613 | S | 4-quinolinium | H | Me | Me | phenyl | H | H | 0 |
| 619 | S | 4-quinolinium | H | Me | —NEt₂ | phenyl | H | H | 0 |
| 621 | S | 4-quinolinium | H | Me | n-butyl | phenyl | H | H | 1 |
| 624 | O | 4-quinolinium | H | Me | n-butyl | phenyl | H | H | 0 |
| 628 | S | 4-quinolinium | H | Me | —OMe | phenyl | H | H | 0 |
| 630 | S | 4-quinolinium | H | Me | phenyl | phenyl | H | H | 0 |
| 633 | O | 4-quinolinium | H | Me | Cl | phenyl | H | H | 0 |
| 634 | S | 4-quinolinium | H | Me | H | n-hexyl | H | H | 0 |
| 637 | O | 4-quinolinium | H | Me | n-butyl | phenyl | H | H | 1 |
| 639 | S | 4-quinolinium | H | Me | phenyl | Me | H | H | 0 |
| 641 | S | 4-quinolinium | H | Me | —SMe | phenyl | H | H | 0 |
| 672 | O | 4-quinolinium | H | Me | —OMe | phenyl | H | H | 1 |
| 720 | S | 4-quinolinium | H | Me | —OEt | phenyl | H | H | 0 |
| 752 | S | 4-quinolinium | H | Me | morpholinyl | Me | H | H | 0 |
| 758 | S | 4-quinolinium | Cl | Me | n-butyl | phenyl | H | H | 0 |
| 760 | S | 4-quinolinium | H | Me | —NEt₂ | phenyl | H | —OMe | 0 |
| 764 | S | 4-quinolinium | H | Me | —O-iPr | phenyl | H | H | 0 |
| 765 | S | 4-quinolinium | H | Me | cyclohexyl | phenyl | H | H | 0 |
| 770 | S | 4-quinolinium | —OMe | Me | H | phenyl | H | H | 0 |
| 774 | S | 4-quinolinium | H | Me | Br | phenyl | H | H | 0 |
| 776 | S | 4-quinolinium | H | Me | —N-nPr₂ | phenyl | H | H | 0 |
| 780 (Cl) | S | 4-quinolinium | H | Me | Cl | cyclohexyl | H | H | 0 |
| 780 (S) | S | 4-quinolinium | H | Me | —SMe | cyclohexyl | H | H | 0 |
| 830 | S | 4-quinolinium | H | Me | Cl | thienyl | H | H | 0 |
| 834 | S | 4-quinolinium | H | Me | F | phenyl | H | H | 0 |
| 835 | S | 4-quinolinium | H | Me | —O-phenyl | phenyl | H | H | 0 |
| 853 | S | 4-quinolinium | H | Me | —S-2-pyridyl | phenyl | H | H | 0 |
| 854 | S | 4-quinolinium | H | Me | —OSO₂CF₃ | phenyl | H | H | 0 |
| 856 | S | 4-quinolinium | H | Me | N—Me-piperazyl | phenyl | H | H | 0 |
| 5103 | S | 4-quinolinium | H | Me | Cl | phenyl | H | —OMe | 0 |
| 6104 | S | 4-quinolinium | H | Me | cyclohexyl | Me | H | H | 0 |

Synthesis

A useful synthetic route to the dyes of the present invention can be described in three parts, following the natural breakdown in the description of the compounds. In general, the synthesis of these dyes requires three precursors: a benzazolium salt, a pyridinium (or quinolinium) salt (both of which have the appropriate chemical substituents), and (where n=1 or 2) a source for the methine spacer. The chemistry that is required to prepare and combine these precursors so as to yield any of the subject derivatives is generally well-understood by one skilled in the art.

The benzazolium moiety.

A wide variety of derivatives of this type for use in preparing photographic dyes have been described, in particular by Brooker and his colleagues (Brooker, et al., J. AM. CHEM. SOC., 64, 199 (1942)). These synthetic precursors have the common structure:

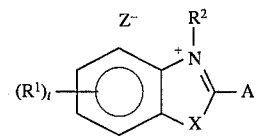

If X is O, the precursor compound is a benzoxazolium; if X is S it is a benzothiazolium; if X is Se it is a benzoselenazolium; if X is N or an alkyl substituted N it is a benzimidazolium; and if X is $CR^{16}R^{17}$ (where $R^{16}$ and $R^{17}$, which may be the same or different, are independently alkyl groups having 1–6 carbons, or $R^{16}$ and $R^{17}$ taken in combination complete a five or six membered saturated ring) then it is an indolinium derivative. The commercial availability of suitable starting materials and relative ease of synthesis make compounds with X=O or S the preferred intermediates.

$R^1$ is usually incorporated in the parent benzazole molecule prior to quaternization with an alkylating agent. $R^2$ is usually obtained by alkylation of the parent heterocycle with an alkylating agent $R^2$-Z where $R^2$ is an alkyl group having 1–6 carbons and Z is an electronegative group that frequently becomes the counterion on the resultant dye. Z⁻ is a biologically compatible counterion that additionally is stable and synthetically accessible. The counterion may be exchanged for another counterion by methods known in the art, such as the use of ion exchange resins or by precipitation.

A is a substituent whose nature is determined by the synthetic method utilized to couple the benzazolium precursor with the pyridinium or quinolinium precursor. When n=0, A is usually alkylthio, commonly methylthio, or A is chloro, bromo or iodo. When n=1 or 2, A is methyl. Only in the case of A=methyl is any part of A incorporated in the final compound.

The pyridinium or quinolinium moiety.

In the synthesis of the dyes of the invention, the second heterocyclic precursor is usually a pyridinium salt that is already appropriately substituted. Less commonly, substituents can be incorporated into the pyridinium structure subsequent to attachment of the benzazolium portion of the dye. One of the substituents, which may be incorporated before or after incorporation of the pyridinium precursor, is an OMEGA.

Aside from the structural differences between pyridines and quinolines, there exist two major structural distinctions within the family of dyes described in the invention, related to the point of attachment of the pyridinium moiety. In one case (where m=0 and p=1) the position of attachment places the methine bridge adjacent to the heterocyclic atom (2-pyridines). In the more common case (where m=1 and p=0) the position of the nitrogen atom is separated from the position of attachment of the methine bridge by what is formally a carbon-carbon double bond $Y_M$ that completes the pyridinium ring (4-pyridines). In all cases m+p=1; that is, if m=1, p=0 and if m=0, p=1.

Typically the required pyridinium salt precursor has the structure

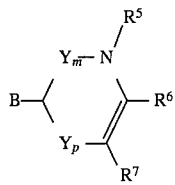

and the quinolinium salt precursor has the general structure

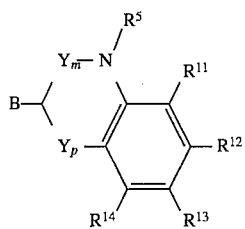

where the ring fragment Y is —CR³=CR⁴—, with subscripts p and m equal to 0 or 1, such that p+m=1. At all times, the ring is a 6 membered pyridinium-based heterocycle.

There are several methods for the synthesis of the pyridinium portion of the dye. As the pyridinium structure contains the greatest possible variation in structure, as well as possible combinations of substituents, several routes to the pyridinium salt are possible, and in fact necessary.

The pyridinium and quinolinium precursors generally can be generated from the corresponding pyridine or quinoline by alkylation at nitrogen using a suitable alkylating agent $R^5$-Z. However, 2- and 4-pyridones and 2- and 4-quinolones are much more versatile chemical intermediates, with the added advantage of being easily prepared. For this reason, the preferred route to the pyridinium or quinolinium precursor will utilizes the corresponding pyridone or quinolone.

Useful methods for generation of the pyridone or quinolone intermediate include:

1) The condensation of an appropriately substituted aniline with diketene or its equivalent, followed by acid cyclization (HETEROCYCLIC COMPOUNDS, VOL. 4, R. C. Elderfield ed., John Wiley and Sons Inc., (1952) pp 1–331).

2) An Ullmann coupling between a 2- or 4-hydroxypyridone, or 2- or 4-hydroxyquinoline and an aryl halide. (Wawzonek et al., J. HETEROCYCLIC CHEM., 25, 381 (1988))

The resulting pyridone or quinolone can be further modified synthetically to create the desired pyridinium or quinolinium precursor by a variety of methods, dependent upon the location of the substituent OMEGA.

The methine bridge.

The methine bridge consists of 1, 3 or 5 methine (—CH=) groups that bridge the benzazolium portion of the molecule and the pyridinium portion in such a way as to permit extensive electronic conjugation. The number of methine groups is determined by the specific synthetic reagents used in the synthesis.

Subsequent modification of dyes

The reactivity of the 2-halogenated pyridinium or quinolinium intermediate offers a variety of synthetic methods for attachment of various substituents at the 2-position. However, the reactivity of the 2-halo derivatives is preserved even after conjugation with the benzazolium precursor, enabling conversion of the resulting dye in which $R^4$ is halogen into the appropriate alkoxy, amino and thiolate analogs, as described above for the pyridinium and quinolinium precursors.

Dye II

The other dye used to perform the viability assay is a fluorescent dye that selectively stains either viable or non-viable cells in the sample (Dye II). A dye selectively stains viable or non-viable cells if, at the concentration used, the fluorescent response of the dye to illumination in viable cells is detectably different from the response of the dye to illumination in non-viable cells. Although a negligible amount of Dye II may enter cells for which Dye II is not selective, the amount should be small enough so that it does not appreciably obscure the fluorescent response due to the binding of Dye I. The difference in response to illumination can be one of fluorescence amplitude, excitation maxima, emission maxima, or other spectral properties or combinations of properties that are detectable by eye or instrumentation. A concentration-dependent response curve can be prepared for any dye to determine a concentration at which the response in viable cells is detectably different from the response in non-viable cells (as for bacteria, in Example 3). Preferably, at the concentration used, the detectable fluorescent response of Dye II is either present or absent.

Dye II is further selected to have spectral characteristics in cells that are detectably different from those of Dye I, such that the fluorescent response of Dye II and Dye I together intracellularly is different from the fluorescent response of Dye I alone. The spectral characteristics determined in solution can serve as a general indication, but where the spectral characteristics are very similar, actual testing in situ will be required. Preferably the dyes are well matched for intensity, but are significantly different in excitation and/or emission spectra; more preferably the dyes have the same or overlapping excitation spectra, but possess visibly different emission spectra. Any detection system can be used to detect the difference in spectral characteristics between the two dyes, including a solid state detector, photomultiplier tube, photographic film, or eye, any of which may be used in conjunction with additional instrumentation such as a spectrometer, microscope, plate reader, fluorescent scanner, flow cytometer, or any combination thereof, to complete the detection system.

Preferably dyes are chosen such that they possess substantially different emission spectra, preferably having emission maxima separated by greater than 10 nm, more preferably having emission maxima separated by greater than 25 nm, even more preferably separated by greater than 50 nm. When differentiation between the two dyes is accomplished by visual inspection, the two dyes preferably have emission wavelengths of perceptibly different colors to enhance visual discrimination. When it is desirable to differentiate between the two dyes using instrumental methods, a variety of filters and diffraction gratings allow the respective emission maxima to be independently detected. When two dyes are selected that possess similar emission maxima, instrumental discrimination can be enhanced by insuring that both dyes' emission spectra have similar integrated amplitudes, similar bandwidths, and the instrumental system's optical throughput be equivalent across the emission range of the two dyes. Instrumental discrimination can also be enhanced by selecting dyes with narrow bandwidths rather than broad bandwidths, however such dyes must necessarily possess a high amplitude emission or be present in sufficient concentration that the loss of integrated signal strength is not detrimental to signal detection.

Because of the wide range of spectral properties to choose from for Dye I, Dye I is typically selected to contrast with the spectral properties of the Dye II and Dye II is selected to be optimal for the selective staining of cells in the sample. Typically, a Dye I that forms a nucleic acid complex that fluoresces red, green or yellow-green will both contrast with the Dye II that is selected and be readily detected by both eye and available intrumentation.

In one aspect of the invention, Dye II gives a detectable fluorescent response in viable cells, but not in non-viable cells. Any dye that gives a fluorescent response detectably different from that of Dye I can be used. A number of fluorescent enzyme substrates and reagents that are known to selectively stain viable cells are available from Molecular Probes, Inc., Eugene, Oreg. A number of such dyes are described in Table 4, reproduced in part from Haugland, Set 25 supra. In addition, the fluorescent products that result from haloalkyl enzyme substrates (Haugland, et al., USE OF HALOALKYL DERIVATIVES OF REPORTER MOLECULES TO ANALYZE METABOLIC ACTIVITY IN CELLS, Int. App. No. WO 93/04192) especially hydrolytic substrates, selectively collect in viable cells where the enzyme is present (See also U.S. Pat. No. 5,208,148 to Naleway, et al., 1993 and U.S. Pat. No. 5,242,805 to Naleway, et al. 1993, both incorporated by reference). Haloalkyl xanthylium mitochondrial stains have also recently been described that selectively collect in viable cells with functioning mitochondria (BioProbes 18, page 7 (1993); Copending patent application Ser. No. 08/143,440, XANTHYLIUM DYES THAT ARE WELL RETAINED IN MITOCHONDRIA, by Haugland et al., Filed Oct. 25, 1993). Typically, a viable cell-selective Dye II is metabolized intracellularly to give a fluorescent product inside viable cells but not inside non-viable cells, such that non-viable cells give the fluorescent response of Dye I alone.

TABLE 4

| Dye | Emission | Specificity | Notes |
| --- | --- | --- | --- |
| Calcein Blue AM | Blue | Esterases | Easily loaded; $T_{1/2}$ probably <15 min |
| Carboxycalcein Blue AM | Blue | Esterases | Easily loaded, $T_{1/2}$ probably <60 min |
| Fluorescein diacetate | Green | Esterases | Easily loaded; poorly retained ($T_{1/2}$ <10 min at 37° C.) |
| Carboxyfluorescein diacetate | Green | Esterases | Moderate retention ($T_{1/2}$ <30 min at 37° C.), pH-sensitive |
| 5-Carboxyfluorescein diacetate AM | Green | Esterases | Moderate retention ($T_{1/2}$ <30 min at 37° C.); more readily loaded than CFDA |
| H$_2$DCF | Green | Peroxidase and esterases | Oxidative, poor retention, pH-insensitive |
| Sulfofluorescein diacetate | Green | Esterases | More difficult to load than CFDA, retention probably better than carboxyfluorescein |
| 5-(and-6)-Carboxy-2',7'-dichloro-fluorescein diacetate | Yellow-green | Esterases | Lower pH-sensitivity than carboxyfluorescein |
| BCECF-AM | Yellow-green | Esterases | Easily loaded, good retention ($T_{1/2}$ up to 1 hour at 37° C.), pH-sensitive |
| Calcein AM | Yellow-green | Esterases | Easily loaded, very good retention ($T_{1/2}$ up to 3 hours at 37° C.), not very pH-sensitive |
| Rhodamine 123 | Yellow-green | Mitochondria | Potential-driver |
| Dihydrorhodamine 123 | Yellow-green | Peroxidases and mitochondria | Oxidative, potential-driven |
| Tetramethylrhodamine ethyl ester | Orange | Mitochondria | Potential-driven |
| Dihydrotetramethyl-rosamine | Orange | Peroxidases and mitochondria | Oxidative, potential-driven |
| Dihydroethidium | Red | Peroxidase-dependent DNA stain | Oxidative, nuclear staining |
| Carboxynaphtho-fluorescein diacetate | Red | Esterases | He-Ne laser-excitable, pH-sensitive |

$T_{1/2}$ is the approximate time during which half of the dye leaks from intact cells. This may depend on the cell type.

In another aspect of the invention, Dye II gives a detectable fluorescent response in non-viable cells, but not in viable cells. Typically, where Dye II is selective for non-viable cells, Dye II is an impermeant dye that only becomes fluorescent upon passing through the cell membrane to bind to some intracellular component, such as an intracellular protein or nucleic acid. Alternatively, Dye II does not stain viable cells because the presence of an intact membrane inhibits access of the dye to intracellular structures, as in the case of a fluorescent-labeled antibody to a protein expressed only intracellularly. Table 5, reproduced in part from Haugland, Sets 25 & 31 supra, describes representative membrane impermeant fluorescent reagents that selectively stain cells with disrupted membranes. While there is not an exact equivalence between an intact cell membrane and the term "viability" (technically defined as the ability of a cell to maintain its existence), it is common to refer to cells where the cell membrane has been irreversibly disrupted as "dead" cells or "non-viable" cells, although they might more accurately be called "membrane-compromised" cells. Loss of the protective cell membrane results in loss of cell structure, loss of critical intracellular contents, loss of essential ionic gradients and loss of electrical potential. The inevitable result of a major loss of membrane integrity is cell death. Where cell death results in the loss of all cell contents, including all intracellular nucleic acids, none of the nucleic acid stains used to practice the invention will label the cellular debris that remains. Where Dye II gives a detectable response in non-viable cells, but not in viable cells, the viable cells are stained with Dye I alone.

TABLE 5

| Dye* | EX max/EM max (nm)** | Kp |
|---|---|---|
| Thiazole orange | 509/525 | $4.8 \times 10^6$ |
| PO-PRO-1 | 435/455 | $2.0 \times 10^6$ |
| BO-PRO-1 | 462/481 | $3.2 \times 10^6$ |
| YO-PRO-1 | 491/509 | $8.2 \times 10^6$ |

TABLE 5-continued

| Dye* | EX max/EM max (nm)** | Kp |
|---|---|---|
| TO-PRO-1 | 515/531 | $2.0 \times 10^7$ |
| PO-PRO-3 | 539/567 | nd |
| BO-PRO-3 | 575/599 | $4.8 \times 10^6$ |
| YO-PRO-3 | 612/631 | $3.3 \times 10^6$ |
| TO-PRO-3 | 642/661 | $6.2 \times 10^6$ |
| POPO-1 | 434/456 | nd |
| BOBO-1 | 462/481 | nd |
| YOYO-1 | 491/509 | $6.0 \times 10^8$ |
| TOTO-1 | 514/533 | $1.1 \times 10^9$ |
| POPO-3 | 534/570 | nd |
| BOBO-3 | 570/602 | nd |
| YOYO-3 | 612/631 | $1.5 \times 10^8$ |
| TOTO-3 | 642/660 | $2.5 \times 10^8$ |
| Ethidium homodimer-1 | 528/617 | $5.0 \times 10^8$ |
| Ethidium homodimer-2 | 535/626 | $1.0 \times 10^9$ |
| Ethidium bromide | 510/595 | $8.3 \times 10^6$ |
| Ethidium monoazide | 465/615 | nd |
| Propidium iodide | 536/617 | $3.8 \times 10^7$ |

*All the PO stains are benzoxazolium-4-pyridinium dyes
BO stains are benzothiazolium-4-pyridinium dyes
YO stains are benzoxazolium-4-quinolinium dyes
TO stains are benzothiazolium-4-quinolinium dyes
**Spectral data are of the dye bound to excess calf thymus DNA (50 bp/dye)
‡The dye's DNA partition coefficient ($K_p$) was determined in a 10% ethanol/water solution by linear fitting of plots of reciprocal fluorescence enhancement versus reciprocal DNA concentration as in Example 11.
nd not determined

TABLE 6

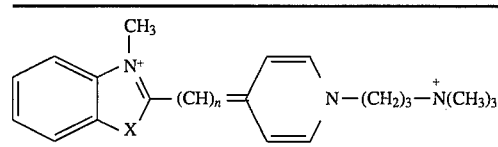

X = S, BO—PRO-n
X = O, PO—PRO-n

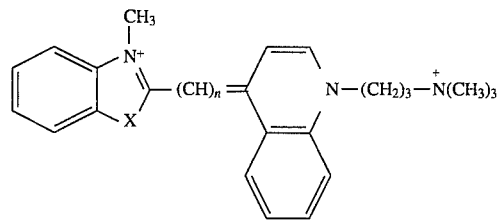

X = S, TO—PRO-n
X = O, YO—PRO-n

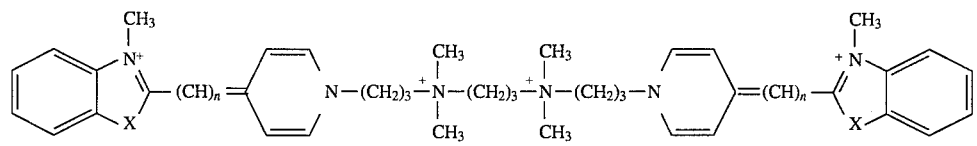

X = S, BOBO-n
X = O, POPO-n

TABLE 6-continued

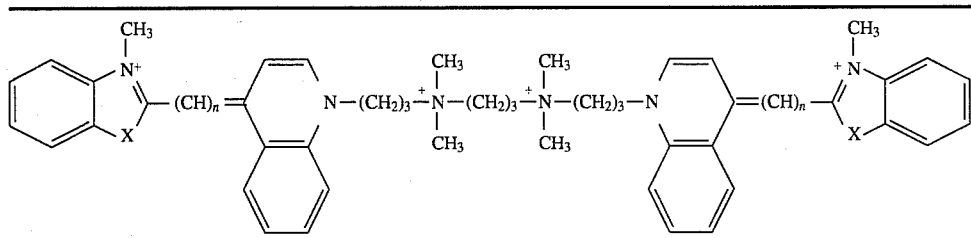

X = S, TOTO-n
X = O, YOYO-n

In one embodiment of the invention, Dye II is a relatively cell-impermeant nucleic acid stain that is a phenanthridium dye, including monomers or dimers thereof, that give an enhanced fluorescence when complexed to intracellular nucleic acids. The intracellular fluorescence resulting from cell-impermeant stains is an indication of membrane disruption and cell death. Examples of impermeant phenanthridium dyes include ethidium homodimer, ethidium bromide, propidium iodide, and other alkyl-substituted phenanthridium dyes except that such $C_{4-10}$ alkyl-substituted dyes have a very low permeability only to live Gram negative organisms, and can be used to determine the viability of such populations, but not where Gram negative microorganisms or other cells indistinguishable by morphology or size alone are present (as described in copending application Ser. No. 08/090,890, now U.S. Pat. No. 5,436,134, Fluorescent Assay for Bacterial Gram Reaction, supra, which is a continuation-in-part of Ser. No. 08/047,683 now abandoned). Generally, phenanthridium dyes complexed with nucleic acids have an emission maximum of between about 580 nm and about 650 nm resulting in an orange-red fluorescent signal in stained cells. In one embodiment, where Dye I emits a green fluorescence and Dye II is a red phenanthridium nucleic acid stain, the sample is preferably illuminated between about 470 nm and 490 nm or between about 300 nm and about 365 nm.

In another embodiment of the invention, Dye II is a relatively cell-impermeant nucleic acid stain that is a a benzazolium dye, such as a benzoxazole, benzimidazole, or benzothiazole, including monomers or dimers thereof, that give an enhanced fluorescence when complexed to intracellular nucleic acids. As with the phenanthridium dyes, the intracellular fluorescence resulting from cell-impermeant stains is an indication of membrane disruption and cell death. Any of the dyes described in patent applications DIMERS OF UNSYMMETRICAL CYANINE DYES (by Yue et al., Int. App. No. WO 93/06482), UNSYMMETRICAL CYANINE DYES WITH CATIONIC SIDE CHAIN (Ser. No. 07/833,006 filed Feb. 8, 1992 by Yue, et al.) now U.S. Pat. No. 5,321,130, and DIMERS OF UNSYMMETRICAL CYANINE DYES CONTAINING PYRIDINIUM MOIETIES (filed Apr. 5, 1993 by Yue et al.) (all three patent applications incorporated by reference) with the desired relative binding affinities and spectral characteristics may be used, including dyes commercially available under the trademarks TOTO, BOBO, POPO, YOYO, TO-PRO, BO-PRO, PO-PRO and YO-PRO from Molecular Probes, Inc., Eugene, Oreg.

The preferred benzazolium dyes have the formula:

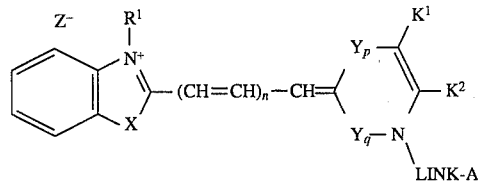

The ring member X is O, S, Se, or $C(CH_3)$. The nitrogen substituent $R^1$ is $C_1$–$C_6$ alkyl, preferably methyl. The methine bridge is either monomethine, trimethine or pentamethine, for n=0, 1 or 2. The aromatic ring component Y is $-CH_2=CH_2-$, with subscripts p and q equal to 0 or 1, such that p+q=1. Ring substituents $K^1$ and $K^2$ may be the same or different, and are independently hydrogen, an alkyl group having 1–6 carbons, or aryl; or $K^1$ and $K^2$ taken in combination complete a 6-membered aromatic ring to yield a quinolinium ring system.

LINK is an aliphatic chain containing a backbone of 4 to 19 methylene groups ($-CH_2-$), which is optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except that where A is H or $CH_3$, LINK must contain at least one N heteroatom. Preferred LINK chains contain two or three heteroatoms, each separated from one another by three methylenes. Preferably the heteroatom is N, where N is substituted by two alkyl groups of 1–6 carbons, which may be the same or different. Preferably LINK contains 12 or less methylene groups.

A is either H, $CH_3$ or is

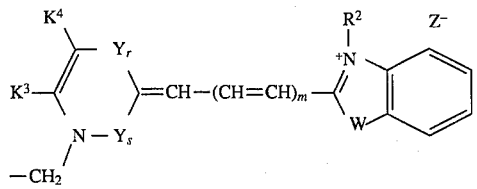

The ring member W is O, S, Se, or $C(CH_3)$. The nitrogen substituent $R^2$ is $C_1$–$C_6$ alkyl, preferably methyl. The methine bridge is either monomethine, trimethine or pentamethine, for m=0, 1 or 2. The aromatic ring component Y is $-CH_2=CH_2-$, with subscripts r and s equal to 0 or 1, such that r+s=1. Ring substituents $K^3$ and $K^4$ may be the same or different, and are independently hydrogen, an alkyl group having 1–6 carbons, or aryl; or $K^3$ and $K^4$ taken in combination complete a 6-membered aromatic ring to yield a quinolinium ring system.

When A is not H or $CH_3$, m and n can be the same or different, and W and X can be the same or different.

Where Dye II is a nucleic acid stain, Dye II must effectively compete for nucleic acid binding, such that the cells for which Dye II is selective are detectable different from the cells for which Dye II is not selective (i.e. cells stained with Dye I alone). Dye II can effectively compete for nucleic acid binding if it has a higher affinity for nucleic acids than does Dye I, if it is used in greater excess, if it has greater access to the nucleic acids, if it has a higher fluorescent yield upon binding, or a combination of these and other factors. Furthermore, Dye II does not have to totally displace Dye I if the combination of the detectable fluorescence from Dye I and Dye II together in cells can still be distinguished from that of Dye I alone in cells. The relative binding affinity of dyes can be compared using by the procedure described in Example 11. Preferably Dye II is also relatively non-fluorescent in the staining solution at the concentration used, but becomes highly fluorescent in combination with the nucleic acids of the cells being analyzed.

Synthesis of Dye II

The large variety of possible Dye II compounds precludes their individual description. However, appropriate Dye II dyes that are phenanthridium derivatives are synthesized according to modification of methods known in the art such as in Watkins, J. CHEM. SOC. 3059 (1952). Dye II compounds that are derivatives of cyanine dyes are commercially available from Molecular Probes, Inc. under the trademarks TOTO™, YOYO™, TO-PRO™, YO-PRO™, PO-PRO™, BO-PRO™, POPO™ and BOBO™ or can be synthesized from similar starting materials according to the procedures of patent applications DIMERS OF UNSYMMETRICAL CYANINE DYES (supra, Ser. No. 07/761177 filed Sep. 16, 1991, now abandoned, by Yue et al.), UNSYMMETRICAL CYANINE DYES WITH CATIONIC SIDE CHAIN (Supra, Ser. No. 07/833,006 filed Feb. 8, 1992, now U.S. Pat. No. 5,321,130 by Yue, et al.), and DIMERS OF UNSYMMETRICAL CYANINE DYES CONTAINING PYRIDINIUM MOIETIES (supra, filed Apr. 5, 1993 by Yue et al.). The preparation of these Dye II dyes closely resembles the preparation of Dye I dyes, as described above. Upon the preparation of an appropriately substituted cyanine dye, the compound is then dimerized, or a cationic side chain attached to generate the desired cell-impermeant nucleic acid stain.

Method of Use

In cells for which Dye II is selective, both Dye I and Dye II are present because Dye I stains all cells, including those for which Dye II is selective. In the cells for which Dye II is selective (and both dyes are present) the intracellular fluorescent response of Dye II is optionally the same as the fluorescent response of Dye II alone (as is the case where Dye II effectively competes for nucleic acid binding relative to Dye I) or a response indicative of the presence of both dyes (as is the case where the competitive binding is less effective or where Dye II is not a nucleic acid stain). The fluorescent response of Dye I alone is indicative of cells for which Dye II is not selective, either viable or non-viable cells as the case may be.

Once the two dyes are selected with the desired combination of spectral characteristics and desired binding affinities, the dyes are added to an aqueous solution that is biologically compatible with the sample of cells to be analyzed, to make an aqueous dye solution, where each dye is present in an effective amount. The dye solution or staining solution is made by dissolving the dye directly in an aqueous solvent such as water, a buffer solution, such as phosphate buffered saline, or an organic water-miscible solvent such as dimethylsulfoxide (DMSO), dimethylformamide (DMF), or a lower alcohol such as methanol or ethanol, or acetonitrile. Dyes that possess low water solubility, including most Dye I dyes, are typically preliminarily dissolved in an organic solvent (preferably DMSO) at a concentration of greater than about 100-times that used in the staining solution, then diluted one or more times with an aqueous solvent such as water or buffer. Preferably, the dye is dissolved in about 100% DMSO and then diluted one or more times in water or buffer such that the dye is present in an effective amount. An effective amount of dye is the amount sufficient to give a detectable fluorescent response in the cells being analyzed. Typically, the concentration of Dye I in the staining solution is greater than about 0.01 μM, and less than about 100 μM, more typically greater than about 1 μM. Typically the concentration of each dye is between about 0.01 μm and about 100 μM. Each dye is optionally prepared in a separate solution or combined in one solution. Generally the dyes are present in the staining solution within about a five-fold molar range, but the molar ratio one to the other in the sample can vary from about 1:1 to about 1:100, and will vary depending on whether the dyes are added to the sample simultaneously or sequentially. It is generally understood in the art that the specific concentration of the staining solution is determined by the physical nature of the sample, and the characteristics of the other dye being used.

The optimal concentration of dye is generally determined according to the cell density. Cell density for discrete cells or microorganisms is determined from a series of absorption readings taken from a serial dilution of a suspension of cells compared with a duplicate plating of cells on an appropriate solid growth medium. The serial dilutions of plated cells are counted and compared with the absorption measurements of the same serial dilutions to determine the relationship between the number of cells or colony forming units per milliliter (cfu/mL) and absorption (cfu/mL/abs). For bacteria, preferably the readings are taken at cell suspension concentrations between about $1 \times 10^3$ cfu/mL and about $1 \times 10^{10}$ cfu/mL, more preferably between about $1 \times 10^5$ cfu/mL and about $1 \times 10^9$ cfu/mL. Below about $10^3$ cfu/mL, absorption readings are not very reliable. In any event, a range of dye concentrations are used to stain the sample or cell suspensions to determine the optimal dye concentration for the cell density of the sample (Example 3). Typically, dye concentrations from about 1 mM down are tested, preferably dye concentrations from about 30 μM down to about 1.1 μM. The tested ranges of dye concentration represent the ranges used for the analysis.

The aqueous dye solution, preferably at the optimal concentration, is combined with a sample of cells to be analyzed. Depending on the type of sample and characteristics of the cells thought to be contained in the sample, the sample is added to the dye solution or the dye solution is added to the sample as required, based on the type of cells, the type of dyes, the preferred staining protocol, or the detection technique. For example, a filter containing a retentate removed from a liquid sample such as water can be placed in the aqueous dye solution, allowing the retentate to incubate in the dye solution (Example 5). Alternatively, where the cells are placed on a slide or in a specialized container, the aqueous dye solution can be added to the slide or container. The dyes can be added in one step or sequentially.

Typically the sample is a bodily fluid such as blood, urine, peritoneal fluid, spinal fluid, lymph fluids, tissue homogenate, mucous, saliva, stool, or physiological secretions or other similar fluids. Alternatively the sample is a fermentation medium such as from a biological reactor or food fermentation process such as brewing. Other sources for samples include environmental sources such as air, soil, or water, for example inline, industrial, or outdoor sources; or surface washes of materials, e.g. food surfaces; or small amounts of solids such as retentates, scrapes, and smears; or liquid growth medium in which cells have been introduced for culturing. The cells are optionally discrete or individual cells, including microorganisms, or multiple cells associated with other cells in two or three dimensional layers, including muticellular organisms, embryos, tissues, biopsies, filaments, biofilms, etc. Cell types include, but are not limited to, eukaryotes, such as nucleated plant and animal cells (Examples 9–10), and prokaryotes, such as bacteria, yeast, and fungi, including mycobacteria and mycoplasma (Examples 5–8). Typically the sample contains prokaryotic cells or animal cells. Samples preferably do not contain plant cells, as plant cells often have less permeant cell walls, and plant cells tend to possess a high degree of autofluorescence. The sample typically contains a mixture of both viable and dead cells.

The viability of a wide variety of Gram negative and Gram positive bacteria can be analyzed, such as bacteria selected from the group consisting of *Bacillus cereus, Bacillus subtilus, Clostridium sporogenes, Corynebacterium xerosis, Micrococcus luteus, Mycobacterium phlei, Propionibacterium freunderreichii, Staphylococcus aureus, Streptococcus pyogenes, Lactobacillus acidophilus, Cytophaga psychrophila, Enterobacter aerogenes, Escherichia coli, Flavobacterium meningosepticum, Klebsiella pneumonia, Neisseria subflava, Pseudomonas aeruginosa, Rhizobium trifolii, Salmonella oranienburg, Shigella sonnei, Vibrio parahaemolyticus* or combinations thereof.

For use in the method of this invention, the cells are optionally in suspension or are immobilized on a solid or semisolid support. In one embodiment of the invention, the cells are in suspension on a microscope slide or in a specialized container needed for an instrumentation detection method such as in a cuvette or in a microtiter plate (e.g. 96 well titer plate). Alternatively, the cells are adhered to a microscope slide using a cell adhesive solution such as poly-L-lysine, or are attached to a filter as a retained residue or retentate.

After the dyes are combined with the sample of cells to be analyzed, either both dyes together or either dye sequentially after the other, the dyes are allowed sufficient time to combine with the cells in the sample before being illuminated to give a detectable fluorescent response. Although some staining with Dye I is detectable almost immediately, staining should generally be allowed to stabilize for at least about 3–5 minutes. Generally, greater than about 10 minutes is sufficient time for the dye(s) to achieve good staining results. Preferably the dye solution is combined with the sample between about 1 minute and about 30 minutes.

The loading time required for Dye I is generally influenced by a number of factors. The loading time is expressed in two ways: as time required to reach half of the maximal fluorescence, $T_{0.5}$ (generally less than 20 seconds, preferably less than 10 seconds), and as the time required to reach 95% of the fluorescence measured at equilibrium, $T_{0.95}$ (generally less than 5 minutes, preferably less than 3 minutes) (see Example 4). Temperature affects a number of different mechanisms that influence cell loading times (see FIG. 1, Example 4), and may also affect the fluorescent response of Dye II to the extent it is dependent on intracellular activity. Preferably, the dye solution is combined with the sample at a temperature optimal for normal activity of the cells in the sample within the operating parameters of the dyes, which fall between about 5° C. and about 50° C. Typically, the optimal temperature for cellular activity is about room temperature (23° C.).

Loading times for impermeant Dye II dyes such as phenanthridium dyes, phenanthridium dimers, or impermeant cyanine dyes is generally the same as those discussed above for Dye I dyes. Cell permeant Dye II dyes selective for viable cells generally require longer loading times, particularly if such dyes require intracellular activity to generate fluorescence.

After sufficient time has elapsed for the dyes to combine with the cells in the sample, the cells are prepared for illumination and observation for the fluorescent response. The dyed cells are prepared for observation by any number of methods known in the art, including placing on microscope slides or in specialized containers for instrument measurements, with or without washing or resuspending cells. Preferably the cells are washed prior to illumination and observation to remove background fluorescence due to growth media or soluble extracellular materials, but washing is not necessary.

Following preparation of the dyed cells, the cells are illuminated at a suitable absorption wavelength. A suitable wavelength is one that comes within the range of absorption wavelengths for each of the fluorescent dyes being used. Typically, the mixture is illuminated by a light source capable of producing light at or near the wavelength of maximum absorption of the dye or dyes, such as by ultraviolet or visible lamp, an arc lamp, a laser, or even sunlight. Preferably the mixture is illuminated at one absorption wavelength shared by both dyes in the aqueous dye solution, where the absorption wavelength is one that will give the brightest fluorescent signal for both of the dyes being used.

Preferably the excitation spectrum of the Dye I-nucleic acid complex overlaps the excitation spectrum of the Dye II or Dye II-nucleic acid complex. More preferably, each dye or dye complexed with nucleic acids has an excitation maximum between about 480 nm and 510 nm.

Factors such as degree of fluorescence enhancement with nucleic acid binding, self quenching, molar extinction coefficient, membrane permeability, intracellular partitioning, nucleic acid binding affinity, and quantum yield contribute to the overall fluorescence of nucleic acid stains in cells. Enhanced cell fluorescence obtained with Dye I is related to unexpected properties other than quantum yield alone. Quantum yield is determined as described above (foot note to Table 2). Normalized quantum yield is determined to illustrate the fold-change in quantum yield of Dye I compared with thiazole orange, a related cell-permeant dye. The normalized fluorescence values represent the quantum yield of each dye divided by the quantum yield of thiazole orange. Fluorescence per cell is also scaled to thiazole orange values for both *E. coli* and *S. aureus* to allow direct comparison between relative (normalized) quantum yield and relative (normalized) fluorescence/cell.

TABLE 7

| Dye | QY | Normalized QY | Normalized Fluorescence/cell (ex 485 nm/em 530 nm) | |
|---|---|---|---|---|
| | | | Escherichia coli | Staphylococcus aureus |
| T.O. | 0.18 | 1.0 | 1 | 1.0 |
| 61 | 0.46 | 2.5 | 5 | 4.7 |
| 63 | 0.24 | 1.3 | 3 | 1.6 |
| 613 | 0.33 | 1.8 | 6 | 3.1 |
| 619 | 0.62 | 3.4 | 13 | 14.7 |
| 624 | 0.58 | 3.2 | 12 | 13.8 |
| 628 | 0.40 | 2.2 | 14 | 10.6 |
| 591 | 0.09 | 0.5 | 1 | 0.9 |
| 634 | 0.18 | 1.0 | 2 | 4.7 |

Illumination of the dyed cells at a suitable wavelength results in one or more illuminated cells that are then analyzed according to their fluorescent response to the illumination. The illuminated cells are observed with any of a number of means for detecting a fluorescent response emitted from the illuminated cells, including but not limited to visible inspection, cameras and film or other imaging equipment, or use of instrumentation such as fluorometers, plate readers, laser scanners, microscopes, or flow cytometers, or by means for amplifying the signal such as a photomultiplier.

The viability of the cells in the sample are then determined based on the fluorescent response that results from illumination. Each of the dyes reacts differently with cells in the sample depending on whether or not the cells are viable. In addition, the determination of viability can be used as a basis for sorting the cells for further experimentation. For example, all cells that "survive" a certain procedure are sorted, or all dead cells in a population are sorted. The cells can be sorted manually or using an automated technique such as flow cytometry according to the procedures known in the art such as in U.S. Pat. No. 4,665,024 to Mansour, et al. (1987) (incorporated by reference).

EXAMPLES

The examples below are given so as to illustrate the practice of this invention. They are not intended to limit or define the entire scope of the invention. As is generally understood in the art, the substituent phenyl (—$C_6H_5$) is represented in the structural formulae as Ø.

Example 1

Preparation of
1,2-Dihydro-4-methyl-1-phenyl-2-quinolone (1)

The following compound is prepared:

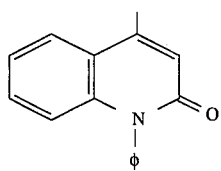

The starting 1,2-dihydro-4-methyl-1-phenyl-2-quinolone (1) is prepared either by an Ullmann coupling according to a literature procedure (e.g. Wawzonek et al. J. HETEROCYCLIC CHEM., 25, 381 (1988)) or via the reaction of the corresponding diarylamine with diketene followed by acid cyclization (e.g. R. C. Elderfield, ed., HETEROCYCLIC COMPOUNDS vol. 4, pp. 1–331, 1952). Thus 10.0 g (62.9 mmoles) of 2-hydroxy-4-methylquinoline is heated at reflux with 24.0 g (377 mmoles) of copper powder, 8.68 g (62.9 mmoles) of potassium carbonate and 19.2 g (94 mmoles) of iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield 8.1 g of the desired product.

Example 2

Preparation of
2-Chloro-4-[2,3-dihydro-3-methyl-(benzo-1,3-thiazol-2-yl)-methylidene]-1-phenylquinolinium iodide (dye 591)

The following compound is prepared:

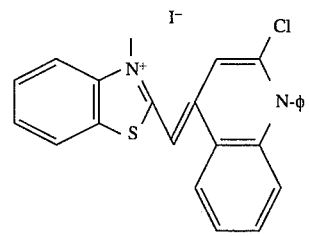

To 2.8 g (11.9 mmoles) of 1,2-dihydro-4-methyl-1-phenyl-2-quinolone (Example 1) in 20 mL of methylene chloride is added, 1.85 g of phosphorus oxychloride and a catalytic amount of dimethylformamide (Marson, TETRAHEDRON, 48, 3659 (1992)). The resulting mixture is heated to reflux for 24 hours. The reaction mixture is cooled to room temperature and 3.5 g (9.6 mmoles) of N-methyl-2-methylthiobenzothiazolium tosylate (Rye, et al., NUCLEIC ACIDS RES., 20, 2803 (1992)) is added followed by 1.3 mL (9.4 mmoles) of triethylamine. The mixture is stirred for an additional 6 hours. The crude product is purified on silica gel using ethyl acetate:chloroform:methanol, 3:3:1 as eluant. The product is then recrystallized from methanol/chloroform/ethyl acetate.

An additional synthetic route to this product utilizes 4-[2,3-dihydro-3-methyl-(benzo-1,3-thiazol-2-yl)-methylidene]-1,2-dihydro-1-phenyl-2-quinolone (4), which in turn is prepared from 1,2-dihydro-4-methyl-1-phenyl-2-quinolone (1) and 3-methyl-2-methylthiobenzothiazolium tosylate. Thus the lithium enolate of the (1) (prepared from treating the quinolone with 2.7 equivalent of lithium diisopropyl amide) or the silyl enolate (from (1) and trimethylsilyl trifluoromethanesulfonate and diisopropylethylamine) is stirred with the benzothiazolium tosylate. The desired intermediate (4) is isolated by column chromatography. The quinolone (4) is then treated with phosphorous oxychloride to generate the 2-chloro derivative.

Example 3

Optimization of Dye Loading

Determination of cell density:

A culture of E. coli is washed by centrifugation and resuspended in water to its original volume. Using Corning 96-well microtiter plates with flat bottoms, 150 μL volumes of suspension are loaded per well. A single well of sterile water is the well background standard. Using a Dynatech MR600 microplate reader equipped with a 410 nm filter, absorbance is determined for the initial volumes of suspension. The suspension is diluted seven times by serial ten-fold dilutions in water, 150 μL of suspension per well, and the absorbance measured for each dilution. Following the absorbance measurements, each dilution loaded into wells is further diluted 1:10 and plated in duplicate on nutrient growth agar. The colonies are counted and expressed as colony forming units per milliliter (cfu/mL). Using the turbidity of the dilution in the microtiter plate, the suspension is diluted to a density of about $1 \times 10^9$ cfu/mL.

Optimization of Staining:

The bacteria suspension, adjusted to a known density as described above, is diluted seven times by serial ten-fold dilutions in water; 150 μL of suspension per well. Three-fold serial dilutions of dye are used (30–0.04 μM); 50 μL of dye at 4× final concentration. Using Corning 96-well microtiter flat-bottom plates, a matrix is set up whereby the cell concentration decreases across the plate and the dye concentration decreases down the plate, final volume per well is 200 μL. The top row and first column are reserved for the control, sterile water. The plate is incubated at 37° C. for 30 minutes, then read in a Millipore Cytofluor™ 2350 96-well fluorescence microplate reader at a fixed excitation of 485+/–10 nm and each of three emission wavelengths, 530+/–12, 620+/–20, or 645+/–20 nm. The results determine the best dye range (30–1 μM) and the best cell concentrations (concentrated through first three ten-fold dilutions) for optimal dye loading. These results lead to the next staining optimization assay. Using the four dye dilutions and the four bacterial dilutions, many bacteria and dyes can be assayed quickly. The data collected allow the determination of optimal dye and cell concentration required for maximal fluorescence intensity per cell.

Example 4

Rate of Dye Loading

Relative rates of dye entry into bacteria:

Half time ($T_{0.5}$) values for dye loading are obtained as follows: Either *E. coli* or *Staph. aureus* are grown in nutrient broth to log phase, washed by centrifugation, and resuspended in water to a density previously shown to allow dye loading to maximal fluorescence/cell. One centimeter pathlength acrylic cuvettes containing 3 mL of cell suspension are placed in a fluorescence spectrophotometer equipped with a temperature regulated cuvette holder and magnetic stirrer. The suspensions are brought to the appropriate temperature prior to dye addition. Millimolar dye stock solutions in DMSO are added at the appropriate concentrations to produce maximum attainable fluorescence/cell at the peak emission wavelength of each dye. The peak fluorescence excitation and emission wavelengths are determined by scanning the spectrum of each dye on similar suspensions of bacteria incubated for 30 min with the dye. Fluorescence intensity of the suspensions is measured at the peak excitation and emission wavelengths (as above) for the dye in each organism. Sampling of fluorescence is carried out at 5 or 10 Hz until the fluorescence signal appears to stabilize.

Effect of temperature on dye loading:

The time required to load two specific embodiments of Dye I and thiazole orange into either *E. coli* or *Staph. aureus* at three different temperatures, 5° C., 23° C., and 37° C. (FIG. 1) is determined by equilibrating the bacterial suspensions at the appropriate temperatures and adding a Dye I stain as described above.

Example 5

Fluorescence Microscopy of Stained Bacteria

Culture conditions and preparation of bacterial suspensions

A bacterial culture is grown to late log phase (typically $10^8$–$10^9$ cfu/mL) in an appropriate nutrient medium. To 1 mL of sterile water in a microfuge tube is added 50 μL of the bacterial culture. The suspension is concentrated by centrifugation in a microfuge for 5 minutes at 10,000 rpm. The supernate is removed, and the pellet is resuspended in 1 mL of sterile, 0.2μ filtered water.

Staining of bacterial suspensions

To the 1 mL bacterial suspension is added 3 μL of a staining solution that is 1.67 mM in dye 624 and 10 mM in propidium iodide, resulting in final suspension concentrations of 5 μM dye 624 and 30 μM propidium iodide. The suspension is mixed thoroughly and incubated at room temperature in the dark for 15 minutes.

Microscopy of a bacterial suspension

A 5 μL aliquot of the stained suspension is trapped between a slide and an 18 mm² coverslip. The slide is observed using a filter set that allows discrimination of the bright green or red fluorescent emissions produced by the staining of live and dead bacteria.

Microscopy of bacteria immobilized on a filter membrane

The stained bacterial suspension is filtered using a 13 mm diameter blackened polycarbonate filter membrane with 0.2 μm pores, used in conjunction with a drain disc support membrane. The bacteria are observed as above.

Microscopy of bacteria immobilized on a glass surface

A 1 mL solution of 0.1 mg/mL>100,000 MW poly-L-lysine is prepared in sterile, filtered water. A 20–30 μL aliquot of the poly-L-lysine solution is then added to the center of a clean glass slide and spread to cover about two-thirds of the surface. The slide is then incubated for 5–10 minutes, after which it is rinsed with sterile water. A 5 μL aliquot of the stained bacterial suspension is applied to the poly-L-lysine coated area of the slide, and a coverslip is placed over the bacteria and sealed with wax or other sealant. The slide is incubated for 5–10 minutes at room temperature in the dark. The bacteria are observed as above.

Example 6

Quantitative Analysis of Bacterial Suspensions Using a Fluorometer

Preparation of standard live and dead bacterial suspensions

Cultures of either *Escherichia coli* or *Staphylococcus aureus* are grown to late log phase in 30 mL of Nutrient Broth (DIFCO 0003-01-6). A 25 mL suspension of the culture is concentrated by centrifugation at 10,000 RCF for 10–15 minutes (RCF=Relative Centrifugal Field in g). The supernate is discarded and the pellet is resuspended by triturating in 2 mL sterile, filtered water. Two 30–40 mL centrifuge tubes are prepared containing, respectively, 20 mL sterile water (for the live bacteria standard) and 20 mL 70% isopropyl alcohol (for the dead bacteria standard). To each of the centrifuge tubes is added 1 mL of the resuspended bacterial sample. Both tubes are then incubated at room temperature for 1 hour, mixing every 15 minutes. Both samples are then centrifuged at 10,000 RCF for 10–15 minutes. The resulting pellets are resuspended as above and centrifuges again. The pellets are then resuspended in separate tubes using 10 mL of sterile water in each tube. The optical density of each suspension is then determined at 670 nm using a 3 mL aliquot in a 1 cm pathlength absorbance cuvette. The optical density of the suspensions is then adjusted to $1\times10^8$ bacteria/mL (0.03 $OD_{670}$) for *E. coli* or $1\times10^7$ bacteria/mL (0.149 $OD_{670}$) for *Staph. aureus*. *Staph. aureus* suspensions are typically 10-fold less concentrated than *E. coli* for fluorometric testing.

Preparation of the calibration curve.

Five different suspensions of live and dead bacteria are prepared in 1 cm acrylic fluorescence cuvettes. The total volume of each of the five samples is 3 mL.

| LIVE/DEAD | mL LIVE | mL DEAD |
|---|---|---|
| 0/100 | 0 | 3.0 |
| 10/90 | 0.3 | 2.7 |
| 50/50 | 1.5 | 1.5 |
| 90/10 | 2.7 | 0.3 |
| 100/0 | 3.0 | 0 |

A sixth cuvette is filled with 3 mL of sterile filtered water to serve as a reagent blank.

A staining solution is prepared that is 1.67 mM in dye 624 and 10 mM in propidium iodide. To each cuvette is added 9 μL of the staining solution, with thorough mixing, resulting in final suspension concentrations of 5 μM dye 624 and 30 μM propidium iodide. The cuvettes are then incubated at room temperature in the dark for 15 minutes.

The fluorescence emission spectrum of each suspension, and the reagent blank, is measured using 470 nm excitation. The integrated intensity of the portion of each spectrum between 510–540 nm (green) and between 620–650 nm (red) is measured, and a ratio of the two intensities is calculated for each suspension.

$$\text{Ratio}_{G/R} = \frac{F_{(green)cell\ suspension} - F_{(green)reagent\ blank}}{F_{(red)cell\ suspension} - F_{(red)reagent\ blank}}$$

Figure 2:
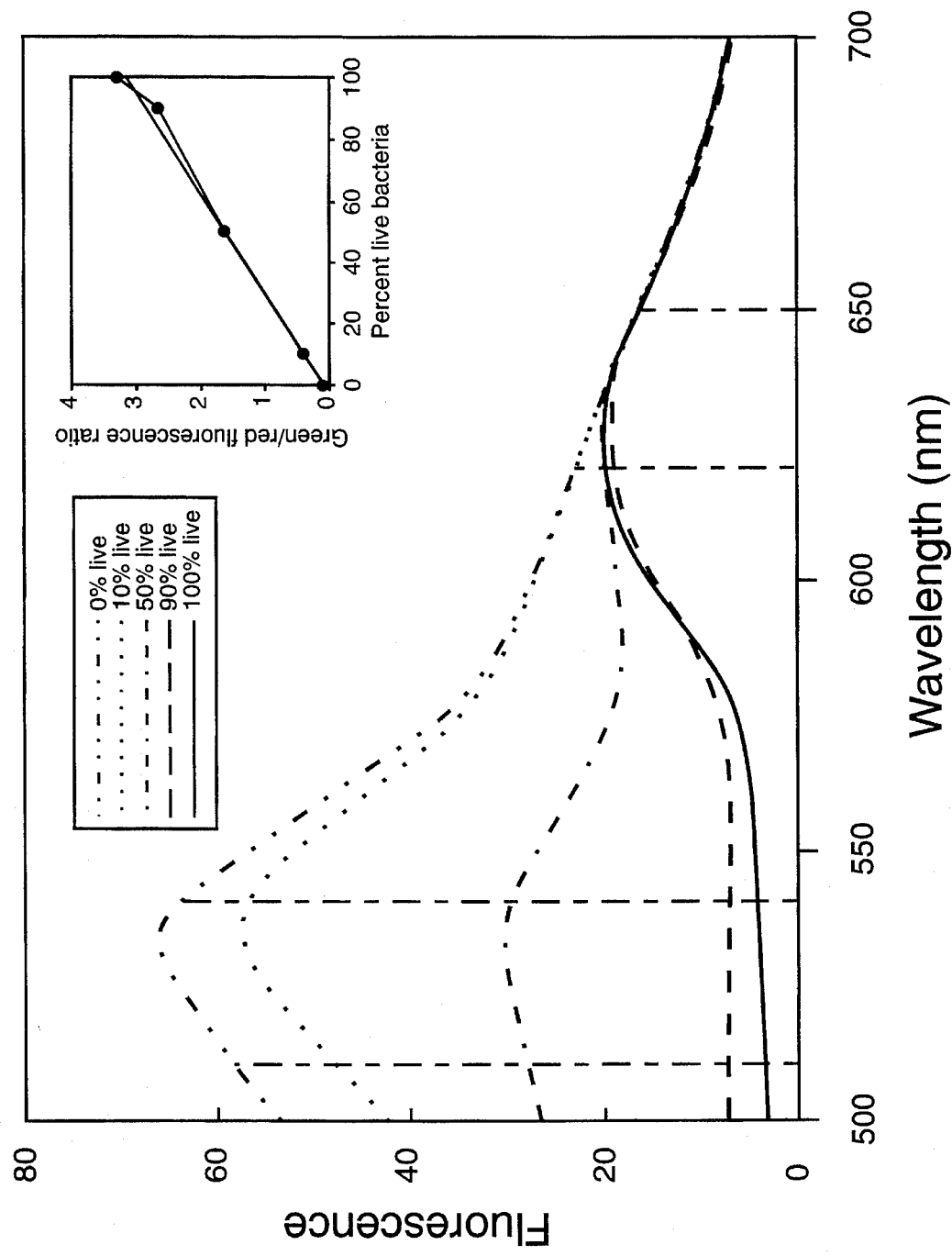
FIG. 2: Fluorescent response of mixed populations of live and dead E. coli when stained with dye 624 and propidium iodide, and the resulting linear calibration curve. S. aureus. (See Example 6).

The ratio of integrated green fluorescence to integrated red fluorescence is plotted versus the percentage of live bacteria to give a linear relationship. This linear plot is then used as a calibration curve for determining live/dead ratios in bacterial samples. The fluorometric response of the mixed live/dead samples, and the resulting calibration curves, are shown in FIG. 2 for *E. coli* and FIG. 3 for *Staph. aureus*.

Example 7

Quantitative Analysis of Mixed Bacterial Suspensions Using a Multi-Well Fluorescence Microplate Reader Preparation of mixed live and dead bacterial suspensions Suspensions of live and dead *E. coli* or *Staph. aureus* are prepared as in Example 6, with the exception that the suspensions are adjusted to an optical density of $1\times10^8$ bacteria/mL (0.03 $OD_{670}$) for *E. coli*, or $5\times10^6$ bacteria/mL (0.074 $OD_{670}$) for *Staph. aureus*. Suspensions of *Staph. aureus* are typically 20-fold less concentrated than *E. coli* for analysis using a Fluorescence Microplate Reader.

Preparation of the calibration curve.

Five different suspensions of live and dead bacteria are prepared in 16×125 mm borosilicate glass culture tubes. The total volume of each of the five samples is 2 mL.

| LIVE/DEAD | mL LIVE | mL DEAD |
|---|---|---|
| 0/100 | 0 | 2.0 |
| 10/90 | 0.2 | 1.8 |
| 50/50 | 1.0 | 1.0 |
| 90/10 | 1.8 | 0.2 |
| 100/0 | 2.0 | 0 |

A sixth culture tube is filled with 2 mL of sterile filtered water to serve as a reagent blank.

A staining solution is prepared that is 1.67 mM in dye 624 and 10 mM in propidium iodide. To 6.6 mL of sterile water in a 16×125 mm borosilicate glass culture tube is added 40 μL of the staining solution, and the new solution is mixed thoroughly.

The mixed live/dead bacterial suspensions are pipetted into each test well of a 96-well flat bottom microplate as follows: The outside wells (rows A and H and columns 1 and 12) are kept empty to avoid spurious readings.

| Row A | columns 2–11 | water blank |
| Row B | columns 2–11 | 0% live bacterial suspension |
| Row C | columns 2–11 | 10% live bacterial suspension |
| Row D | columns 2–11 | 50% live bacterial suspension |
| Row E | columns 2–11 | 90% live bacterial suspension |
| Row F | columns 2–11 | 100% live bacterial suspension |
| Row G | columns 2–11 | reagent blank |
| Row H | columns 2–11 | water blank |

Using a new pipet tip for each row, 100 μL of the diluted staining solution is pipetted into each appropriate well in the row. The plate is then incubated in the dark for 15 minutes.

The appropriate gain setting and filters are set on the specific fluorescence microplate reader used as below:

| | Excitation (blue) | Emission 1 (green) | Emission 2 (red) |
|---|---|---|---|
| Millipore ® Cytofuor ™ 2350 | 485 ± 20 nm | 530 ± 25 nm | 620 ± 40 nm |

The excitation filter is set to blue Excitation (as above) and the emission filter is set to Emission 1. The fluorescence emission intensity of the entire plate is measured, and the data saved. The emission filter is set to Emission 2, retaining the blue excitation filter setting. The fluorescence emission intensity of the entire plate is measured, and the data saved. The fluorescence data are analyzed by subtracting the fluorescence of the reagent solution in water from the fluorescence of the stained cell suspensions with each filter combination and dividing the corrected fluorescence emission at Emission 1 by the fluorescence emission at Emission 2.

$$\text{Ratio}_{G/R} = \frac{F_{(green)cell\ suspension} - F_{(green)reagent\ blank}}{F_{(red)cell\ suspension} - F_{(red)reagent\ blank}}$$

The corrected $\text{Ratio}_{G/R}$ versus percent live bacteria suspension is plotted to give a linear standard calibration. This linear plot is then used as a calibration curve for determining live/dead ratios in bacterial samples.

Example 8

Quantitative Analysis of Bacterial Suspensions Using Flow Cytometry

Preparation of standard live and dead bacterial suspensions

Standard live and dead suspensions of *E. coli* are prepared as described in Example 6. The 1×10$^8$ bacteria/mL (0.03 OD$_{670}$) suspensions are then diluted 1:100 in sterile water to give a final bacterial density of 1×10$^6$ bacteria/mL for both bacterial samples. Eleven different proportions of *E. coli* are prepared in 16×125 mm borosilicate glass tubes according to the table below. The volume of each bacterial sample is 2 mL.

| LIVE/DEAD | mL LIVE | mL DEAD |
|---|---|---|
| 0/100 | 0 | 2.0 |
| 10/90 | 0.2 | 1.8 |
| 20/80 | 0.4 | 1.6 |
| 30/70 | 0.6 | 1.4 |
| 40/60 | 0.8 | 1.2 |
| 50/50 | 1.0 | 1.0 |
| 60/40 | 1.2 | 0.8 |
| 70/30 | 1.4 | 0.6 |
| 80/20 | 1.6 | 0.4 |
| 90/10 | 1.8 | 0.2 |
| 100/0 | 2.0 | 0 |

A staining solution is prepared that is 1.67 mM in dye 624 and 10 mM in propidium iodide. Each of the 11 samples is stained with 6 µL of the staining solution and mixed thoroughly. The samples are incubated in the dark for 15 minutes.

Analysis by Flow Cytometry

The bacterial samples are analyzed using an EPICS flow cytometer (Coulter Electronics, Hialeah, Fla.) equipped with a 400 mW argon laser (488 nm excitation), two photomultipliers (PMT), and a 76 µm flow tip. Data acquisition and analysis are controlled using CICERO software and hardware interface (Cytomation). The emission light path contains a 515 nm blocking filter, 590 nm dichroic filter before the Green PMT, and a 610 nm absorbance filter before the Red PMT. The sampling rate of the bacterial suspension is ~300 particles/sec and the sheath fluid is distilled water.

The fluorescence acquisition was gated on the log integrated green fluorescence (LIGFL) and discriminated at the 15% level on LIGFL since both live and dead bacteria have a measurable green signal. The populations of bacteria were discriminated as three regions of the LIRFL vs. LIGFL plot and the numbers of bacteria found within these regions were used to determine the percentage of viable organisms in the population. The resulting calibration curve is then corrected to match the theoretical value by inclusion of a correction factor (the % dead bacteria present in the "live" bacteria populations required to make the experimental 100% LIVE value match the theoretical 100% LIVE value) (See FIG. 4a)–4b)).

Example 9

Differentiation Between Live and Dead Primary Culture Lymphocytes

Peripheral blood lymphocytes are isolated from whole goat blood using the standard ficoll density gradient protocol. The cells are incubated in saline buffer with coverslips coated with a cell adhesive. After attachment to the coverslip, the cells are incubated with either a) 1 µM dye 637 for 30 minutes followed by washing, and subsequently incubating with 1 µM calcein AM for 30 minutes, or b) as above but labeling first with calcein AM, and subsequently staining with dye 637.

After washing with saline, the stained cells are viewed through a long-pass fluorescein filter to view calcein fluorescence and a long-pass Texas Red® filter to view the emission of dye 637. A Nikon fluorescence microscope equipped with a 40× objective is used for inspection and photography.

The majority of cells are visible using both the red and green filters. Cells that are dead, however, are stained only with dye 637 and do not exhibit green fluorescence. Both batches of cells exhibit this differential staining, regardless of order of staining.

Example 10

Differentiation Between Live and Dead Cells From a Fibroblast Cell Line

NIH/3T3 mouse fibroblast cell line is obtained from American Type Culture Collection Co., Rockville, Md. The cells are maintained in a humidified atmosphere of 5% CO$_2$ in Dulbecco's modified Eagle's medium (DMEM) supplemented with 10% calf serum, 50 µg/mL gentamicin, 300 µg/mL L-glutamine and 10 mM HEPES pH 7.4. Cells are subcultured every 3 days by trypsinization using 0.05% trypsin and 0.02% EDTA in a Ca- and Mg-free saline solution (Gibco BRL, Gaithersburg, Md.).

A 5 µM staining solution of the dye 61 is prepared by dilution of 25 µL of 2 mM stock solution into 10 mL DMEM. A 2 µM staining solution of ethidium homodimer-1 is prepared by dilution of 2 µL of 10 mM stock solution into 10 mL phosphate buffered saline (PBS).

The 3T$_3$ cells are stained with the 5 µM solution of dye 61, and then incubated in the dark at room temperature for 30 minutes. The cells are then washed with the 2 µM ethidium homodimer-1 solution.

The 3T$_3$ cells are then observed a long-pass fluorescein filter to view dye 61 fluorescence and a long-pass Texas Red® filter to view the emission of ethidium homodimer. A Nikon fluorescence microscope equipped with a 40× objective is used for inspection and photography. Live and dead cells are differentiated by red and green fluorescence, where live cells are stained fluorescent green (dye 61) while dead cells are stained fluorescent red (ethidium homodimer-1).

Example 11

Calculation of Dye/Nucleic Acid Affinity

Incremental amounts of calf thymus DNA in a binding buffer (10 mM phosphate pH 7.0 with 1 mM EDTA and 100 mM NaCl) are added to 0.22 µM and 0.1 µM solutions of the nucleic acid dye of interest in 10% ethanol, keeping concentrations constant. The fluorescence intensity (F) determined in a fluorescence plate reader (CytoFluor from Millipore Corporation), is measured versus DNA concentration expressed in terms of base pairs concentration (B). In all the titrations, [Dye]/[Base Pair] is always larger than 3 to fulfill the requirements of the partition model.

The nucleic acid/water partition coefficient ($K_p$) representing the relative affinity of the dye for DNA is calculated from the fluorescence data according to the following formula:

$$\frac{1}{F} = \left[ \frac{5.6 \times 10^7}{K_p F_0} \right] \left[ \frac{1}{B} \right] + \frac{1}{F_0}$$

where $5.6 \times 10^7$ (μM) is water molar concentration; B is the concentration of base pairs; and $F_0$ is the fluorescence enhancement at saturation.

It is to be understood that, while the foregoing invention has been described in detail by way of illustration and example, numerous modifications, substitutions, and alterations are possible without departing from the spirit and scope of the invention as described in the following claims.

We claim:

1. A method of analyzing cell viability, comprising:
   a) combining a sample of cells with an aqueous dye solution comprising a fluorescent Dye I of the formula:

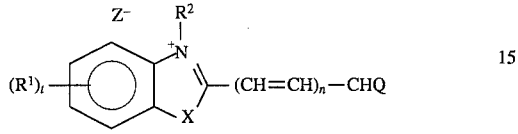

where t=1–4 and each $R^1$, which may be the same or different, is H, $C_{1-6}$ alkyl; trifluoromethyl; halogen; or —$OR^8$, —$SR^8$ or —$(NR^8R^9)$ where $R^8$ and $R^9$, which can be the same or different, are independently H; $C_{1-6}$ alkyl; or 1–2 alicyclic, heteroalicyclic, aromatic, or heteroaromatic rings having a total of 3–16 ring atoms wherein the heteroatoms are O, N or S; or $R^8$ and $R^9$ taken in combination are —$(CH_2)_2$—L—$(CH_2)_2$— where L=a single bond or —$CH_2$—, —O—, or —$NR^{10}$, where $R^{10}$ is H or $C_{1-6}$ alkyl;

$R^2$ is $C_{1-6}$ alkyl;

$Z^-$ is a biologically compatible counterion;

X is O; S; Se; or $NR^{15}$, where $R^{15}$ is H or $C_{1-6}$ alkyl; or $CR^{16}R^{17}$, where $R^{16}$ and $R^{17}$, which may be the same or different, are independently H or $C_{1-6}$ alkyl, or the carbons of $R^{16}$ and $R^{17}$ taken in combination complete a five or six membered saturated ring;

n=0, 1, or 2;

Q has the formula Q1 or Q2

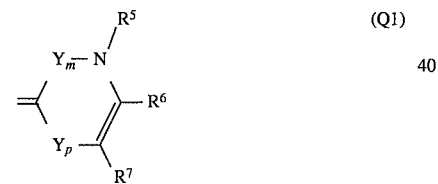

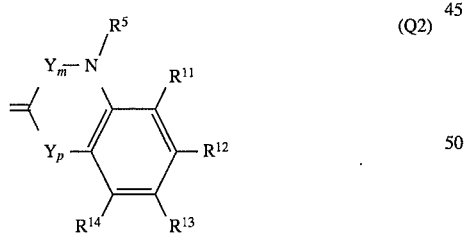

wherein

Y is —$CR^3$=$CR^4$—; p and m=0 or 1, such that p+m=1;

$R^5$ is a $C_{1-6}$ alkyl, $C_{1-6}$ alkenyl, $C_{1-6}$ polyalkenyl, $C_{1-6}$ alkynyl or $C_{1-6}$ polyalkynyl group; or $R^5$ is an OMEGA;

$R^3$, $R^4$, $R^6$ and $R^7$, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or halogen; or —$OR^8$, —$SR^8$, —$(NR^8R^9)$, as defined previously; or —$OSO_2R^{19}$ where $R^{19}$ is $C_{1-6}$ alkyl, or $C_{1-6}$ perfluoroalkyl, or aryl; or an OMEGA; or $R^6$ and $R^7$, taken in combination are —$(CH_2)_v$— where v=3 or 4, or $R^6$ and $R^7$ form a fused aromatic ring according to formula Q2;

$R^{11}$, $R^{12}$, $R^{13}$, and $R^{14}$, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or a halogen; or an OMEGA; or —OH, —$OR^8$, —$SR^8$, or —$(NR^8R^9)$;

OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms wherein the heteroatoms are O, N or S, that is unsubstituted or optionally substituted one or more times, independently, by halogen, alkyl, perfluoroalkyl, amino, alkylamino, dialkylamino, alkoxy or carboxyalkyl, having 1–6 carbons, and that is attached as $R^3$, $R^4$, $R^5$, $R^6$, $R^7$, $R^{11}$, $R^{12}$, $R^{13}$, or $R^{14}$ by a single bond;

such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different;

and a fluorescent Dye II that selectively stains either viable or non-viable cells, where Dye II and Dye I together intracellularly have a detectable fluorescent response in combination with cells in the sample that is different from a fluorescent response of Dye I alone, and where Dye I and Dye II are each present in an amount sufficient to give a detectable fluorescent response, resulting in a sample of stained cells;

b) illuminating the sample of stained cells at a suitable absorption wavelength that results in one or more illuminated cells; and c) observing the illuminated cells with means for detecting a fluorescent response resulting from illumination.

2. A method, as claimed in claim 1, wherein Dye I has the formula:

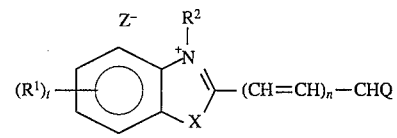

where t=1 and $R^1$ is H, $C_{1-6}$ alkyl; trifluoromethyl; halogen; or —$OR^8$, —$SR^8$ or —$(NR^8R^9)$ where $R^8$ and $R^9$, which can be the same or different, are independently H or $C_{1-6}$ alkyl;

X is O or S;

Q has the formula Q1 or Q2

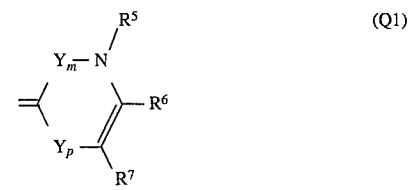

-continued

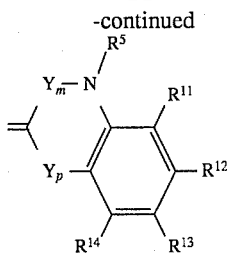

(Q2)

wherein p=0 and m=1; and

OMEGA is a saturated or unsaturated, substituted or unsubstituted, cyclic substituent that has a total of 4–6 ring carbon atoms in an alicyclic, heteroalicyclic, aromatic, or heteroaromatic ring, containing 1–2 heteroatoms wherein the heteroatoms are O, N or S, that is unsubstituted or optionally substituted one or more times, independently, by halogen or by alkyl or alkoxy having 1–6 carbons, and that is attached as $R^3$, $R^4$, $R^5$, $R^6$, $R^7$, $R^{11}$, $R^{12}$, $R^{13}$, or $R^{14}$ by a single bond.

3. A method, as claimed in claim 1, wherein Dye I has the formula:

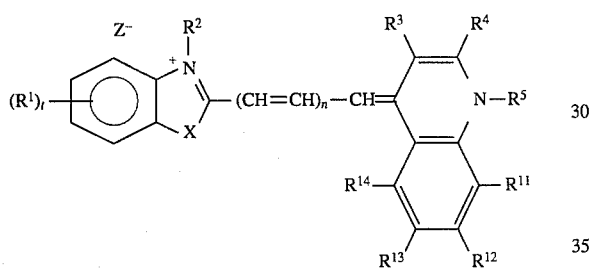

wherein t=1 and $R^1$ is H; or a $C_{1-2}$ alkyl; or a trifluoromethyl; or a halogen; or $-OR^8$, $-SR^8$ or $-(NR^8R^9)$ where $R^8$ and $R^9$, which can be the same or different, are independently H or $C_{1-4}$ alkyl;

$R^3$, $R^4$, $R^5$, $R^{11}$, $R^{12}$, $R^{13}$, and $R^{14}$ are independently H, halogen, $C_{1-6}$ alkyl, $-OR^8$, $-SR^8$, $-(NR^8R^9)$, where $R^8$ and $R^9$, which may be the same or different, are independently H; or alkyl groups having 1–6 carbons; or 1–2 substituted or unsubstituted alicyclic, heteroalicyclic, aromatic, or heteroaromatic rings, containing 1–4 heteroatoms, wherein the heteroatoms are O, N, or S; or $R^8$ and $R^9$ taken in combination are $-(CH_2)_2-L-(CH_2)_2-$ where L=$-O-$, $-NR^{10}-$, $-CH_2-$ or a single bond where $R^{10}$ is H or an alkyl group having 1–6 carbons; or $-OSO_2R^{19}$ where $R^{19}$ is alkyl having 1–6 carbons or perfluoroalkyl having 1–6 carbons or aryl; or an OMEGA;

X is O or S; and at least one of $R^4$ and $R^5$ is an OMEGA.

4. A method, as claimed in claim 1, further comprising sorting the cells based on their fluorescent response.

5. A method of analyzing cell viability, comprising:

a) combining a sample of cells with an aqueous dye solution comprising an effective amount of a fluorescent Dye I of the formula:

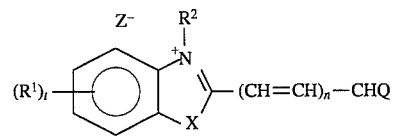

where t=1–4 and each $R^1$, which may be the same or different, is H, $C_{1-6}$ alkyl; trifluoromethyl; halogen; or $-OR^8$, $-SR^8$ or $-(NR^8R^9)$ where $R^8$ and $R^9$, which can be the same or different, are independently H; $C_{1-6}$ alkyl; or 1–2 alicyclic, heteroalicyclic, aromatic, or heteroaromatic rings having a total of 3–16 ring atoms wherein the heteroatoms are O, N or S; or $R^8$ and $R^9$ taken in combination are $-(CH_2)_2-L-(CH_2)_2-$ where L=a single bond or $-CH_2-$, $-O-$, or $-NR^{10}$, where $R^{10}$ is H or $C_{1-6}$ alkyl;

$R^2$ is $C_{1-6}$ alkyl;

$Z^-$ is a biologically compatible counterion;

X is O; S; Se; or $NR^{15}$, where $R^{15}$ is H or $C_{1-6}$ alkyl; or $CR^{16}R^{17}$, where $R^{16}$ and $R^{17}$, which may be the same or different, are independently H or $C_{1-6}$ alkyl, or the carbons of $R^{16}$ and $R^{17}$ taken in combination complete a five or six membered saturated ring;

n=0, 1, or 2;

Q has the formula Q1 or Q2

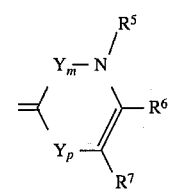

(Q1)

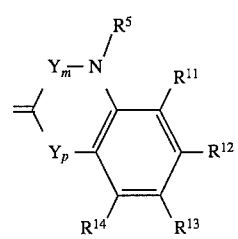

(Q2)

wherein

Y is $-CR^3=CR^4-$; p and m=0 or 1, such that p+m=1;

$R^5$ is a $C_{1-6}$ alkyl, $C_{1-6}$ alkenyl, $C_{1-6}$ polyalkenyl, $C_{1-6}$ alkynyl or $C_{1-6}$ polyalkynyl group; or $R^5$ is an OMEGA;

$R^3$, $R^4$, $R^6$ and $R^7$, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or halogen; or $-OR^8$, $-SR^8$, $-(NR^8R^9)$, as defined previously; or $-OSO_2R^{19}$ where $R^{19}$ is $C_{1-6}$ alkyl, or $C_{1-6}$ perfluoroalkyl, or aryl; or an OMEGA; or $R^6$ and $R^7$, taken in combination are $-(CH_2)_v-$ where v=3 or 4, or $R^6$ and $R^7$ form a fused aromatic ring according to formula Q2;

$R^{11}$, $R^{12}$, $R^{13}$, and $R^{14}$, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or a halogen; or an OMEGA; or $-OH$, $-OR^8$, $-SR^8$, or $-(NR^8R^9)$;

OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms wherein the heteroatoms are O, N or S, that is unsubstituted or optionally substituted one or more times, independently, by halogen, alkyl, perfluoroalkyl, amino, alkylamino, dialkylamino, alkoxy or carboxyalkyl, having 1–6 carbons, and that is attached as $R^3$, $R^4$, $R^5$, $R^6$, $R^7$, $R^{11}$, $R^{12}$, $R^{13}$, or $R^{14}$ by a single bond;

such that at least one of $R^3$, $R^4$, $R^5$, $R^6$, $R^7$, $R^{11}$, $R^{12}$, $R^{13}$, and $R^{14}$ is an OMEGA, and, where more than one of $R^3$, $R^4$, $R^5$, $R^6$, $R^7$, $R^{11}$, $R^{12}$, $R^{13}$, and $R^{14}$ is an OMEGA, each OMEGA is optionally the same or different;

and an effective amount of a fluorescent Dye II that selectively stains only viable cells, where Dye II and Dye I together have a detectable fluorescent response in combination with cells in the sample that is different from a fluorescent response of Dye I alone, resulting in a sample of stained cells;

b) illuminating the sample of stained cells at a suitable absorption wavelength that results in one or more illuminated cells; and c) observing the illuminated cells with means for detecting a fluorescent response resulting from illumination, where non-viable cells show the fluorescent response of Dye I alone.

6. A method, as claimed in claim 5, wherein Dye I has the formula:

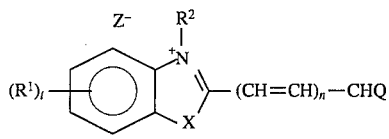

where t=1 and $R^1$ is H, $C_{1-6}$ alkyl; trifluoromethyl; halogen; or —$OR^8$, —$SR^8$ or —($NR^8R^9$) where $R^8$ and $R^9$, which can be the same or different, are independently H or $C_{1-6}$ alkyl;

X is O or S;

Q has the formula Q1 or Q2

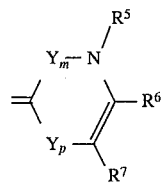 (Q1)

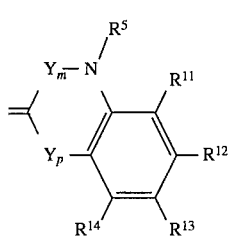 (Q2)

wherein p=0 and m=1; and

Dye II is a fluorogenic compound that becomes fluorescent in response to reaction with an intracellular enzyme.

7. A method, as claimed in claim 6, where Dye I has the formula:

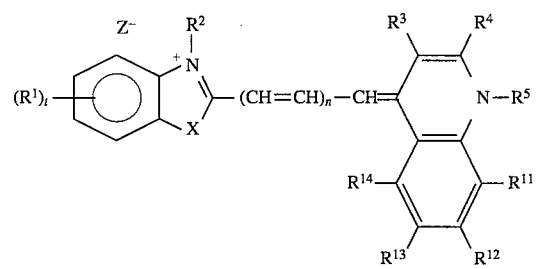

wherein $R^1$ is H; $R^2$ is methyl or ethyl; X is O or S; n=0 or 1;

$R^3$, $R^{11}$, $R^{12}$, $R^{13}$, and $R^{14}$ are H;

$R^4$ is H, halogen, $C_{1-6}$ alkyl, —$OR^8$, —$SR^8$, —($NR^8R^9$), where $R^8$ and $R^9$, which may be the same or different, are independently H; or alkyl groups having 1–6 carbons; or 1–2 substituted or unsubstituted alicyclic, heteroalicyclic, aromatic, or heteroaromatic rings, containing 1–4 heteroatoms, wherein the heteroatoms are O, N, or S; or $R^8$ and $R^9$ taken in combination are —$(CH_2)_2$—L—$(CH_2)_2$— where L=—O—, —$NR^{10}$—, —$CH_2$— or a single bond where $R^{10}$ is H or an alkyl group having 1–6 carbons; or —$OSO_2R^{19}$ where $R^{19}$ is alkyl having 1–6 carbons or perfluoroalkyl having 1–6 carbons or aryl; or an OMEGA; and $R^5$ is phenyl.

8. A method of analyzing cell viability, comprising:

a) combining a sample of cells with an aqueous dye solution comprising a fluorescent Dye I of the formula:

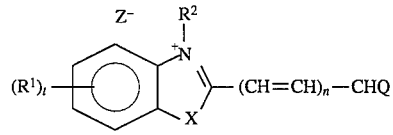

where t=1–4 and each $R^1$, which may be the same or different, is H, $C_{1-6}$ alkyl; trifluoromethyl; halogen; or —$OR^8$, —$SR^8$ or —($NR^8R^9$) where $R^8$ and $R^9$, which can be the same or different, are independently H; $C_{1-6}$ alkyl; or 1–2 alicyclic, heteroalicyclic, aromatic, or heteroaromatic rings having a total of 3–16 ring atoms wherein the heteroatoms are O, N or S; or $R^8$ and $R^9$ taken in combination are —$(CH_2)_2$—L—$(CH_2)_2$ — where L=a single bond or —$CH_2$—, —O—, or —$NR^{10}$, where $R^{10}$ is H or $C_{1-6}$ alkyl;

$R^2$ is $C_{1-6}$ alkyl;

$Z^-$ is a biologically compatible counterion;

X is O; S; Se; or $NR^{15}$, where $R^{15}$ is H or $C_{1-6}$ alkyl; or $CR^{16}R^{17}$, where $R^{16}$ and $R^{17}$, which may be the same or different, are independently H or $C_{1-6}$ alkyl, or the carbons of $R^{16}$ and $R^{17}$ taken in combination complete a five or six membered saturated ring;

n=0, 1, or 2;

Q has the formula Q1 or Q2

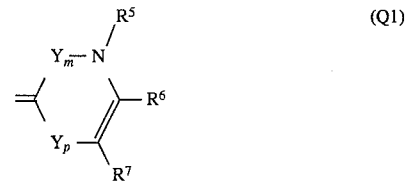 (Q1)

-continued

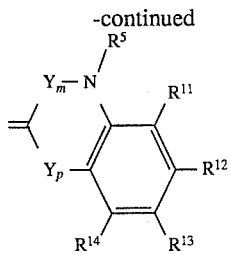
(Q2)

wherein
Y is —CR³=CR⁴—; p and m=0 or 1, such that p+m=1;
R⁵ is a $C_{1-6}$ alkyl, $C_{1-6}$ alkenyl, $C_{1-6}$ polyalkenyl, $C_{1-6}$ alkynyl or $C_{1-6}$ polyalkynyl group; or R⁵ is an OMEGA;
R³, R⁴, R⁶ and R⁷, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or halogen; or —OR⁸, —SR⁸, —(NR⁸R⁹), as defined previously; or —OSO₂R¹⁹ where R¹⁹ is $C_{1-6}$ alkyl, or $C_{1-6}$ perfluoroalkyl, or aryl; or an OMEGA; or R⁶ and R⁷, taken in combination are —(CH₂)ᵥ— where v=3 or 4, or R⁶ and R⁷ form a fused aromatic ring according to formula Q2;
R¹¹, R¹², R¹³, and R¹⁴, which may be the same or different, are independently H; or a $C_{1-6}$ alkyl, $C_{1-6}$ alkenyl, $C_{1-6}$ polyalkenyl, $C_{1-6}$ alkynyl or $C_{1-6}$ polyalkynyl group; or a halogen; or an OMEGA; or —OH, —OR⁸, —SR⁸, or —(NR⁸R⁹);
OMEGA is a saturated or unsaturated, substituted or unsubstituted, cyclic substituent that has a total of 2–16 ring carbon atoms in 1–2 alicyclic, heteroalicyclic, aromatic, or heteroaromatic rings, containing 1–4 heteroatoms wherein the heteroatoms are O, N or S, that is unsubstituted or optionally substituted one or more times, independently, by halogen, alkyl, perfluoroalkyl, amino, alkylamino, dialkylamino, alkoxy or carboxyalkyl, having 1–6 carbons, and that is attached as R³, R⁴, R⁵, R⁶, R⁷, R¹¹, R¹², R¹³, or R¹⁴ by a single bond;
such that at least one of R³, R⁴, R⁵, R⁶, R⁷, R¹¹, R¹², R¹³, and R¹⁴ is an OMEGA, and, where more than one of R³, R⁴, R⁵, R⁶, R⁷, R¹¹, R¹², R¹³, and R¹⁴ is an OMEGA, each OMEGA is optionally the same or different;
and a fluorescent Dye II that selectively stains only non-viable cells, such that Dye II and Dye I together have a detectable fluorescent response in combination with cells in the sample that is different from a fluorescent response of Dye I alone, and where Dye I and Dye II are each present in an amount sufficient to give a detectable fluorescent response, resulting in a sample of stained cells;

b) illuminating the sample of stained cells at a suitable absorption wavelength that results in one or more illuminated cells; and c) observing the illuminated cells with means for detecting a fluorescent response resulting from illumination, where viable cells show the fluorescent response of Dye I alone.

9. A method, as in claim 8, where Dye II is a cell-impermeant nucleic acid stain with a binding affinity for nucleic acids greater than that of Dye I.

10. A method, as claimed in claim 8, where Dye II is a phenanthridium dye.

11. A method, as claimed in claim 8, where Dye II is a benzazolium dye.

12. A method, as claimed in claim 8, wherein Dye I has the formula:

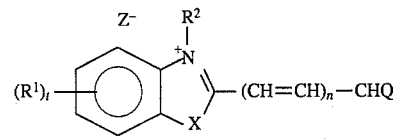

where t=1 and R¹ is H, $C_{1-6}$ alkyl; trifluoromethyl; halogen; or —OR⁸, —SR⁸ or —(NR⁸R⁹) where R⁸ and R⁹, which can be the same or different, are independently H or $C_{1-6}$ alkyl;

X is O or S;

Q has the formula Q1 or Q2

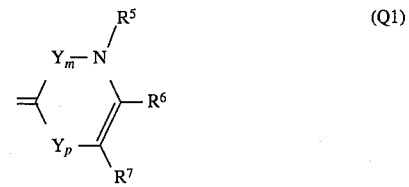
(Q1)

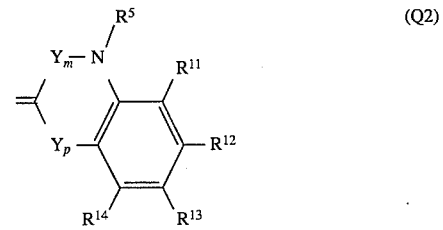
(Q2)

wherein p=0 and m=1; and

OMEGA is a saturated or unsaturated, substituted or unsubstituted, cyclic substituent that has a total of 4–6 ring carbon atoms in an alicyclic, heteroalicyclic, aromatic, or heteroaromatic ring, containing 1–2 heteroatoms wherein the heteroatoms are O, N or S, that is unsubstituted or optionally substituted one or more times, independently, by halogen or by alkyl or alkoxy having 1–6 carbons, and that is attached as R³, R⁴, R⁵, R⁶, R⁷, R¹¹, R¹², R¹³, or R¹⁴ by a single bond; and Dye II is a cell-impermeant nucleic acid stain.

13. A method, as in claim 12, where the sample comprises gram negative and gram positive bacteria.

14. A method as claimed in claim 12, where the sample contains bacteria, which may be the same or different, selected from the group consisting of *Bacillus cereus, Bacillus subtilus, Clostridium sporogenes, Corynebacterium xerosis, Micrococcus luteus, Mycobacterium phlei, Propionibacterium freunderreichii, Staphylococcus aureus, Streptococcus pyogenes, Lactobacillus acidophilus, Cytophaga psychrophila, Enterobacter aerogenes, Escherichia coli, Flavobacterium meningosepticum, Klebsiella pneumonia, Neisseria subflava, Pseudomonas aeruginosa, Rhizobium trifolii, Salmonella oranienburg, Shigella sonnei, Vibrio parahaemolyticus* or combinations thereof.

15. A method, as in claim 8, where the dyes are present in concentrations between about 0.01 μM and about 100 μM.

16. A method, as in claim 8, where the stained cells are illuminated at a wavelength between about 480 nm and about 510 nm.

17. A method, as claimed in claim 8, wherein the sample comprises animal cells.

18. A method, as claimed in claim 8, wherein Dye I has the formula:

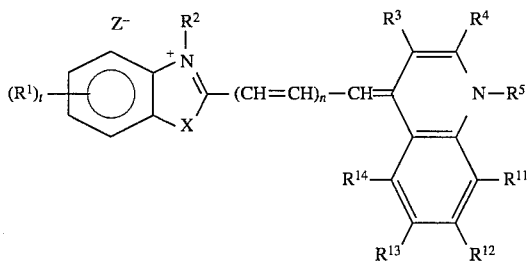

wherein $R^1$ is H;
$R^2$ is methyl or ethyl;
X is O or S;
n=0 or 1;
$R^3$, $R^{11}$, $R^{12}$, $R^{13}$, and $R^{14}$ are H;
$R^4$ is H, halogen, $C_{1-6}$ alkyl, —$OR^8$, —$SR^8$, —($NR^8R^9$), where $R^8$ and $R^9$, which may be the same or different, are independently H; or alkyl groups having 1–6 carbons; or 1–2 substituted or unsubstituted alicyclic, heteroalicyclic, aromatic, or heteroaromatic rings, containing 1–4 heteroatoms, wherein the heteroatoms are O, N, or S; or $R^8$ and $R^9$ taken in combination are —$(CH_2)_2$—L—$(CH_2)_2$— where L=—O—, —$NR^{10}$—, —$CH_2$— or a single bond where $R^{10}$ is H or an alkyl group having 1–6 carbons; or —$OSO_2R^{19}$ where $R^{19}$ is alkyl having 1–6 carbons or perfluoroalkyl having 1–6 carbons or aryl; or an OMEGA; and
$R^5$ is phenyl.

19. A method, as claimed in claim 18, where Dye II is a benzazolium dye of the formula:

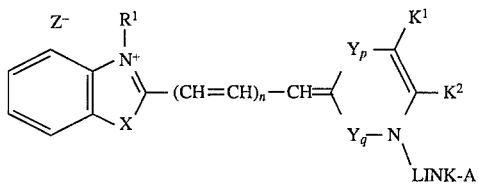

wherein
X is O, S, Se, or C(CH$_3$); and
$R^1$ is an alkyl group of 1–6 carbons;
n=0, 1 or 2;
Y is —$CH_2$=$CH_2$—;
p and q are equal to 0 or 1, such that p+q=1;
$K^1$ and $K^2$ may be the same or different, and are independently hydrogen, an alkyl group having 1–6 carbons, or aryl; or $K^1$ and $K^2$ taken in combination complete a 6-membered aromatic ring;
LINK is an aliphatic chain containing a backbone of 4 to 19 methylene groups (—$CH_2$—), optionally interspersed at one or more intervals with a heteroatom, each of which is independently N, O or S, wherein each N heteroatom is additionally substituted by 1–2 H, or 1–2 alkyl groups with 1 to 6 carbons, which alkyl substituents may be the same or different, provided that any heteroatom is separated from another heteroatom by at least 2 methylene groups, wherein one methylene terminus of LINK is attached to a nitrogen atom of the pyridinium or quinolinium heterocycle and another methylene terminus of LINK is attached to A, except where A is H or CH$_3$, LINK must contain at least one N heteroatom;
A is H, CH$_3$ or is

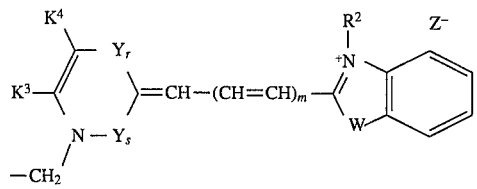

wherein
W is O, S, Se, or C(CH$_3$);
$R^2$ is an alkyl group of 1–6 carbons;
m=0, 1 or 2;
Y is —$CH_2$=$CH_2$—;
r and s equal to 0 or 1, such that r+s=1;
$K^3$ and $K^4$ may be the same or different, and are independently hydrogen, an alkyl group having 1–6 carbons, or aryl; or $K^3$ and $K^4$ taken in combination complete a 6-membered aromatic ring.

20. A method, as claimed in claim 18, where Dye II is a propidium or ethidium or an ethidium dimer and, in the formula of Dye I, n=0.

* * * * *

UNITED STATES PATENT AND TRADEMARK OFFICE
CERTIFICATE OF CORRECTION

PATENT NO. : 5,534,416
DATED : July 9 1996
INVENTOR(S) : Millard, et. Al.

It is certified that error appears in the above-identified patent and that said Letters Patent is hereby corrected as shown below:

In the drawings, Sheet 2, Fig. 2, the figure legend should appear as follows:

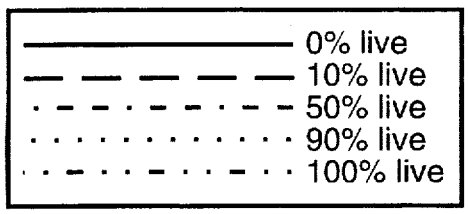

Figure 3:
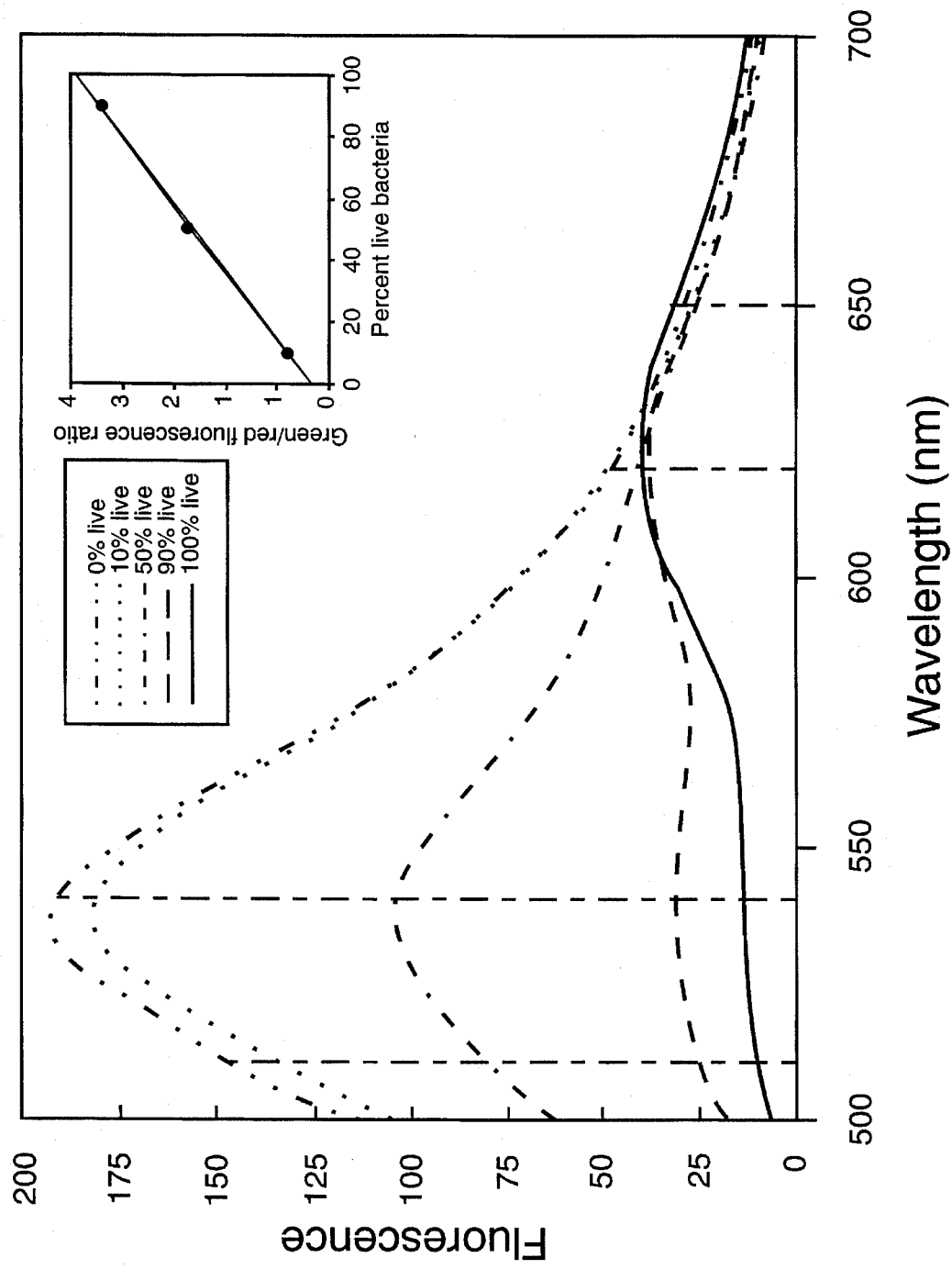
FIG. 3: Fluorescent response of mixed populations of live and dead S. aureus when stained with dye 624 and propidium iodide, and the resulting linear calibration curve. (See Example 6).

In the drawings, Sheet 3, Fig. 3, the figure legend should appear as follows:

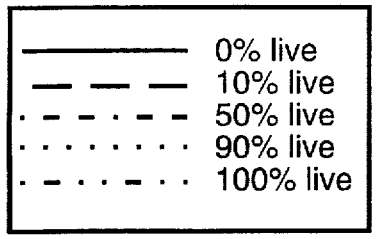

UNITED STATES PATENT AND TRADEMARK OFFICE
CERTIFICATE OF CORRECTION

PATENT NO. : 5,534,416
DATED : July 9, 1996
INVENTOR(S) : Millard, et al

It is certified that error appears in the above-identified patent and that said Letters Patent is hereby corrected as shown below:

At column 34, line 45, "$C_{1\infty6}$ alkyl" should be --$C_{1-6}$ alkyl--.

Signed and Sealed this

Third Day of March, 1998

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO.   : 5,534,416
DATED        : July 9, 1996
INVENTOR(S)  : Paul J. Millard, L. Roth, Stephen T. Yue and Richard P. Haugland It is certified that error appears in the above-identified patent and that said Letters Patent is hereby corrected as shown below:

<u>Title page,</u>
Notice field, " Pat. No. 5,372,842" should read -- Pat. No. US 5,545,535. --

Signed and Sealed this

Eighteenth Day of June, 2002

*Attest:*

*Attesting Officer*

JAMES E. ROGAN
*Director of the United States Patent and Trademark Office*